(12) United States Patent
Madsen et al.

(10) Patent No.: US 9,371,308 B2
(45) Date of Patent: Jun. 21, 2016

(54) POLYMERIC PHOTOINITIATORS

(75) Inventors: Niels Joergen Madsen, Alleroed (DK); Petr Sehnal, York (GB); Christian B. Nielsen, København (DK); David George Anderson, York (GB)

(73) Assignee: Coloplast A/S, Humlebaek (DK)

( * ) Notice: Subject to any disclaimer, the term of this patent is extended or adjusted under 35 U.S.C. 154(b) by 197 days.

(21) Appl. No.: 13/885,007

(22) PCT Filed: Nov. 11, 2011

(86) PCT No.: PCT/DK2011/050431
§ 371 (c)(1),
(2), (4) Date: Jul. 1, 2013

(87) PCT Pub. No.: WO2012/062333
PCT Pub. Date: May 18, 2012

(65) Prior Publication Data
US 2013/0289155 A1   Oct. 31, 2013

(30) Foreign Application Priority Data

Nov. 12, 2010 (DK) .................................. 2010 70487
Dec. 22, 2010 (DK) .................................. 2010 70572
Jan. 26, 2011 (DK) .................................. 2011 70044
Jan. 26, 2011 (DK) .................................. 2011 70047

(51) Int. Cl.

| | | |
|---|---|---|
| *C07D 213/02* | (2006.01) | |
| *C07D 221/00* | (2006.01) | |
| *C07D 207/416* | (2006.01) | |
| *C07D 335/16* | (2006.01) | |
| *C08F 2/50* | (2006.01) | |
| *C08G 18/32* | (2006.01) | |
| *C08G 18/48* | (2006.01) | |
| *C08G 18/50* | (2006.01) | |
| *C08G 18/73* | (2006.01) | |
| *C08G 18/75* | (2006.01) | |
| *C07C 217/22* | (2006.01) | |
| *C07C 225/16* | (2006.01) | |
| *C07C 225/22* | (2006.01) | |
| *C08J 3/24* | (2006.01) | |
| *C08J 3/28* | (2006.01) | |
| *C09D 175/12* | (2006.01) | |
| *C07C 213/02* | (2006.01) | |
| *C07C 221/00* | (2006.01) | |
| *C07C 217/62* | (2006.01) | |

(52) U.S. Cl.
CPC ............ *C07D 335/16* (2013.01); *C07C 213/02* (2013.01); *C07C 217/22* (2013.01); *C07C 217/62* (2013.01); *C07C 221/00* (2013.01); *C07C 225/16* (2013.01); *C07C 225/22* (2013.01); *C07D 207/416* (2013.01); *C08F 2/50* (2013.01); *C08G 18/3275* (2013.01); *C08G 18/4833* (2013.01); *C08G 18/5024* (2013.01); *C08G 18/73* (2013.01); *C08G 18/758* (2013.01); *C08J 3/24* (2013.01); *C08J 3/28* (2013.01); *C09D 175/12* (2013.01); *C08J 2375/00* (2013.01)

(58) Field of Classification Search
CPC .... C07D 335/16; C07D 207/416; C08F 2/50; C08G 18/3275; C08G 18/4833; C08G 18/5024; C08G 18/73; C08G 18/758; C08C 217/22; C08C 225/16; C08C 225/22; C08C 213/02; C08C 221/00; C08C 217/62; C08J 3/24; C08J 3/28; C08J 2375/00; C09D 175/12
See application file for complete search history.

(56) References Cited

U.S. PATENT DOCUMENTS

| | | |
|---|---|---|
| 4,602,097 A | 7/1986 | Curtis |
| 4,861,916 A | 8/1989 | Koehler et al. |
| 6,031,044 A | 2/2000 | Kokel et al. |
| 2007/0078246 A1 | 4/2007 | Herr et al. |
| 2010/0049146 A1 | 2/2010 | Nielsen et al. |

FOREIGN PATENT DOCUMENTS

| | | |
|---|---|---|
| CN | 1817914 | 8/2006 |
| CN | 101012180 | 8/2007 |
| CN | 101029095 | 9/2007 |
| CN | 101495162 | 7/2009 |
| JP | H10182781 | 7/1998 |
| WO | WO 96/33156 | 10/1996 |
| WO | WO 97/49664 | 12/1997 |
| WO | WO 98/51759 | 11/1998 |
| WO | WO 03/033492 | 4/2003 |
| WO | WO 2007/092935 | 8/2007 |
| WO | WO 2009/060235 | 5/2009 |

(Continued)

OTHER PUBLICATIONS

Office Action mailed on Aug. 28, 2014 in U.S. Appl. No. 13/805,134.
Polymer Synthesis: Theory and Practice, Fundamentals, Methods, Experiments, 4th Edition, 2005, Springer pp. 319-324.
Wei et al. "Novel PU-type polymeric photoinitiator comprising side-chain benzophenone and coinitiator amine for photopolymerization of PU acrylate." Polymers for Advanced Technologies, vol. 19, No. 12, Jan. 1, 2008, pp. 1763-1770.
Wei et al. "Novel Polymeric, Thio-Containing Photoinitiator Comprising In-Chain Benzophenone and an Amine Coinitiator for Photopolymerization." Journal of Polymer Science: Part A: Polymer Chemistry, vol, 45, pp. 576-587.
Wei et al. "Novel Photosensitive Thio-Containing Polyurethane as Macophotoinitiator Comprising Side-Chain as Benzophenone and Co-Initiator Amine for Photopolymerization." Macromolecules, vol. 40, 2007, pp. 2344-2351.

(Continued)

*Primary Examiner* — Sanza McClendon
(74) *Attorney, Agent, or Firm* — Coloplast Corp., Coloplast A/S; Nick Baumann

(57) ABSTRACT

A polymeric photoinitiator, most suitably a polyurethane photoinitiator, is obtained by step-growth co-polymerization of at least one monomer (A) with at least one monomer (B). Monomer (A) includes a photoinitiator moiety, while monomer (B) is a monomer reactive with monomer (A) to form a polymer. A method produces the polymeric photoinitiator, a method cross-links the polymeric photoinitiator, and the polymeric photoinitiator is used as a photoinitiator of radical polymerization.

45 Claims, No Drawings

(56) References Cited

FOREIGN PATENT DOCUMENTS

| WO | WO 2010/063612 | 6/2010 |
|---|---|---|
| WO | WO 2010/069758 | 6/2010 |
| WO | WO 2011/160641 | 12/2011 |

OTHER PUBLICATIONS

Wei et al. "Novel Highly Efficient Macrophotoinitiator Comprising Benzophenone, Conitiator Amine, and Thio Moieties for Photopolymerization." Macromolecules, vol. 42, 2009, pp. 5486-5491.
Corrales et al. "Free radical macrophotoinitiators: an overview on recent advances." Journal of Photochemistry and Photobiology Part A: Chemistry 159 (2003) pp. 103-114.
Gilbert et al. "Essentials of Molecuar Photochemistry", Angew. Chem., 103 (1991) Nr. 11, p. 1554-1555.
Gould et al. "Novel Self-Initiating UV-Curable Resins: Generation Three," Proceedings from RadTech Europe 05, vol. 1, Oct. 18-20, 2005, p. 245-251.
Nguyen et al. "Malemide Reactive Oligomers" Proceedings from RadTech Europe 03, vol. 1, Nov. 3-5, 2003, pp. 589-594.
Naskar et al. "UV assisted stabilization routes for carbon fiber precursors produced from melt-processible polyacrylonitrile terpolymer." Carbon 43 (2005), pp. 1065-1072.
Mukundan et al. "A photocrosslinkable melt processible acrylonitrile terpolymer as carbon fiber precursor," Polymer 47 (2006), pp. 4163-4171.
Fouassier "Excited-State Reactivity in Radical Polymerisation Photoinitiators" in Radiation Curing in Polymer Science and Technology. Ch. 1, pp. 1-61, 1993.
Kopeinig et al. "Further Covalently Bonded Photoinitiators" Proceedings from RadTech Europe 05, vol. 2, Oct. 18-20, 2005; pp. 375-381.
Rampa et al. "Acetylcholinesterase Inhibitors: SAR and Kinetic Studies on ω-[$N$-Methyl-$N$-(3-alkylcarbamoyloxyphenyl)methyl]aminoalkoxyaryl Derivatives." J. Med. Chem. 2001, 44, 3810-3820.
Rampa et al. "Acetycholinesterase-Inhibitors: Synthesis and Structure-Activity Relationships of ω-[$N$-Methyl-$N$-(3-alkylcarbamoyloxyphenyl)-methyl]aminoalkoxyheteroaryle Derivatives." J. Med. Chem, 1998, 41, 3976-3986.
Walsh et al. "Synthesis and Antiallergy Activity of 4-(Diarylhydroxymethyl)-1-[3-(aryloxy)propyl]piperidines and Structurally Related Compounds." J. Med. Chem. 1989, 32, 105-118.
Podgorsek et al. "Environmentally benign electrophilic and radical bromination 'on water': $H_2O_2$-HBR system versus $N$-bromosuccinimide," Tetrahedron 65 (2009) 4429-4439.
Gravatt et al. "DNA-Directed Alkylating Agents. 4. 4-Anilinoquinoline-Based Minor Groove Directed Aniline Mustards." J. Med. Chem. 1991, 34, 1552-1560.
El Sayed et al. "Linear solvation energy (LSE) correlations of the solvatochromic response and x-ray structure analysis of hydrophilically $N$-substituted Michler's ketone derivatives," Journal of Physical Organic Chemistry, 2001; 14: 247-255.
Griffiths at al. "Surface functional polymers by post-polymerization modification, release and regeneration of hydrogen peroxide and bacterial activity." Langmuir, vol. 26, Jul. 30, 2010, pp. 14142-14153.
Yang et al. "Amine-linked Thioxanthones as water-compatible photoinitiators." Journal of Polymer Science: Part A: Polymer Chemistry, vol. 36, Jan. 1, 1998, pp. 2563-2570.
Temel et al. "Photopolymerization and photophysical properties of amine linked benzophenone photoinitiator for free radical polymerization." Journal of Photochemistry and Photobiology, vol. 219, No. 1, Jan. 21, 2011, pp. 26-31.
Polymer Synthesis: Theory and Practice, Fundamentals, Methods, Experiments, 4th edition, Springer, 319-324.
Peinado et al. "Synthesis of novel 2-(3'dialkylaminopropoxy)-thioxanthone derivatives. Photochemistry and evalusation as photoinitiators of butyl acrylate ploymerization" European Polymer Journal, vol. 28, No. 10, Oct. 1, 1992, pp. 1315-1320.

POLYMERIC PHOTOINITIATORS

This is a national stage of PCT/DK11/050431 filed Nov. 11, 2011 and published in English, which has a priority of Denmark no. PA 2010 70487 filed Nov. 12, 2010, Denmark no. PA 2010 70572 filed Dec. 22, 2010, Denmark no. PA 2011 70047 filed Jan. 26, 2011, and Denmark no. PA 2011 70044 filed Jan. 26, 2011, hereby incorporated by reference.

FIELD OF THE INVENTION

The present invention relates to novel polymeric photoinitiators. The polymeric photoinitiators incorporate photoinitiator moieties as pendant groups on the polymeric backbone.

BACKGROUND OF THE INVENTION

Curing of coatings through ultraviolet (UV) radiation requires efficient methods of initiating the chemical reaction responsible for the curing process. Curing of polymeric material through generation of radical species upon irradiation with UV light is widely used to produce coatings for medical devices. The paint and lacquer industry also makes use of UV-initiated curing of acrylates, where photoinitiators in many cases are employed. These two examples illustrate the diversity of UV curable coatings.

Until recently, polymers designed for use in coatings have relied on photoinitiators with relatively low molecular weight to initiate polymerization (curing). In addition, polymerization reactions often comprise co-reagents and catalysts of the polymerization process which also have relatively low molecular weight. Low molecular weight substances, and their by-products in the polymerization reaction, are generally difficult to remove from the resultant polymer, but instead remain within the polymer matrix and diffuse slowly to the surface of the polymer during its lifetime. Over time, low molecular weight substances therefore leach from the polymer into the surrounding environment.

This presents particular problems in the polymers used in the medical field, as patient safety considerations limit the amount and type of substance which can leach from a given polymer. This is especially relevant if the polymer is to be used as a coating or adhesive which is designed to be in contact with the inside or outside of the patient's body. Notably, certain low molecular weight co-reagents and catalysts of polyurethane polymerization are toxic to plants and animals (e.g. dibutyltin dilaurate (DBTDL) or 1,4-diazabicyclo [2.2.2]octane (DABCO)).

Higher molecular weight photoinitiators, in particular polymeric photoinitiators, have comparably higher intrinsic viscosities which most likely result in longer diffusion times through a matrix. Migration of the UV active substances to the surface is therefore diminished when polymeric photoinitiators are used as opposed to lower molecular weight photoinitiators. Scarce literature within the field of polymeric photoinitiators suggests that development of such polymers could lead to novel applications and present solutions for existing needs, such as providing a material with negligent migration of substances to the surface/patient.

Some descriptions of polymeric photoinitiators are found in scientific literature, where for example 4-amino-4'-[4-aminothiophenyl]benzophenone is polymerized with toluene-2,4-diisocyanate (J. Wei, H. Wang, J. Yin J. *Polym. Sci., Part A: Polym. Chem.*, 45 (2007), 576-587; J. Wei, H. Wang, X. Jiang, J. Yin, *Macromolecules*, 40 (2007), 2344-2351). Examples of the use of this photoinitiator to polymerize acrylates are also given in this work. A similar strategy is also discussed in J. Wei, F. Liu *Macromolecules*, 42 (2009), 5486-2351, where 4-[(4-maleimido)thiophenyl]benzophenone was synthesized and polymerized into a macromolecular photoinitiator.

A variety of polymeric photoinitiators other than benzophenone based structures are discussed in T. Corrales, F. Catalina, C. Peinado, N. S. Allen *Journal of Photochemistry and Photobiology A: Chemistry*, 159 (2003), 103-114.

US 2007/0078246 describes different aromatic ketone systems which are substituted on a siloxane polymeric chain.

Benzophenone derivatives with pendant alkyl ether substituents have been described in WO 96/33156. Similar structures are described in WO 98/51759 where benzophenone derivatives with pendant alkyl ether groups are presented. A related type of photoinitiator class is described in WO 2009/060235, where thioxanthone moieties are attached to an oligomeric backbone.

Several photoinitiators (e.g. benzophenone, anthraquinone) with pendant polyalkyl ethers are described in WO 97/49664.

WO 03/033492 discloses thioxanthone derivatives attached to a polyhydroxy residue.

U.S. Pat. No. 4,602,097 details water-soluble photoinitiators where two photoinitiator moieties are bridged together by a polyalkylether of sufficient length to make it water soluble.

Many of the prior art references disclose photoinitiators which are end-substituted onto a polymeric entity. However, the photoefficiency of such substances is limited, as they are large molecular weight molecules comprising comparatively little photoinitiator per unit mass.

U.S. Pat. No. 4,861,916 discloses photoinitiators for the photopolymerization of ethylenically unsaturated compounds, in particular in aqueous systems.

EP 2130817 discloses polymerizable Type II photoinitiators. Radiation curable compositions and inks including the multifunctional Type II photoinitiator are also disclosed.

Despite previous efforts, there remains a need for novel photoinitiators which can reduce by-products of low molecular weight in a polymerization process, particularly polymerization to form polyurethanes. In addition, it would prove useful to reduce or completely remove the need for low molecular weight polymerization catalysts or co-reagents in the polymerization process.

The present invention provides polymer photoinitiators in which the photoinitiator moiety itself becomes an integral part of the polymer, and remains so, during and after the polymerization process. Leaching of photoinitiator and photoinitiator by-products is therefore reduced or even eliminated.

At the same time, the particular design of the photoinitiator monomer allows a reduction in the amount of or even the elimination of co-reagents and catalysts in the polymerization process. In that such substances are minimised or eliminated, their concentrations in the resulting polymers are also reduced, so that leaching of such substances is correspondingly reduced or eliminated. Polymers likely to improve medical safety are thereby obtained.

SUMMARY OF THE INVENTION

It is an object of embodiments of the invention to provide a polymeric photoinitiator, being a co-polymer of at least one monomer (A) with at least one monomer (B), wherein:
monomer (A) is a photoinitiator monomer (A) of the formula (I):

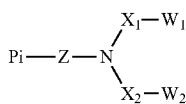

(I)

in which:

Pi is a photoinitiator moiety;

Z is a linker moiety;

$X_1$ and $X_2$ are independently selected from optionally substituted $C_1$-$C_{12}$ alkylene, optionally substituted $C_1$-$C_{12}$ alkenylene, optionally substituted heterocyclyl, —O—, —S—, —NR$^2$—, —C(=O)—, —C(=NR$^2$)—, —Si(R$^2$)$_2$—O—, optionally substituted aryl, and combinations thereof, wherein R$^2$ is H or optionally substituted $C_1$-$C_{12}$ alkyl;

wherein $X_1$ and $X_2$ or a part thereof may be linked to one another or to Z to form one or more ring structures;

wherein Z, $X_1$ and $X_2$ are selected such that N is a tertiary amine;

$W_1$ and $W_2$ are functional groups independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups;

monomer (B) comprises at least two functional groups $W_3$ and $W_4$, said $W_3$ and $W_4$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups;

wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

Co-polymerization using photoinitiator moieties having the general formula (I) are able to at least partially replace nucleophilic low molecular weight amine catalysts (e.g. DABCO) in polyurethane polymerization processes. The physical and chemical properties of the polymeric photoinitiators of the present invention can be tailored as required, e.g. by varying the relative amounts and the nature of each monomer (A) or (B).

Furthermore, the invention provides a method for producing the polymeric photoinitiator, a method of cross-linking the polymeric photoinitiator by means of UV radiation and/or heat, and the use of the polymeric photoinitiator as a photoinitiator of radical polymerization.

Further aspects of the invention are presented in the dependent claims.

DETAILED DISCLOSURE OF THE INVENTION

Definitions

In the following, when a part of a molecule is described as "optionally substituted" it is meant that said part may be substituted by one or more substituents selected from: $C_1$-$C_6$ linear, branched or cyclic alkyl, aryl, —OH, —CN, —NO$_2$, halogens, amines, amides, alcohols, ethers, thioethers, sulfones and derivatives thereof, sulfoxides and derivatives thereof, carbonates, isocyanates, nitrates and acrylates.

The term "heterocyclyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "alkylene" is used in the following to specify moieties derived from alkanes in which two H atoms have been removed to form a diradical species. The simplest alkylene is methylene —CH$_2$—, and other alkylenes include ethylene —CH$_2$—CH$_2$—, propylene —C$_3$H$_6$— and butylene —C$_4$H$_8$—. The term "alkylene" includes branched, linear and cyclic alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "alkenylene" is used in the following to specify moieties derived from alkenes in which two H atoms have been removed to form a diradical species. Examples include ethenylene —CH$_2$=CH$_2$— and propenylene —C$_3$H$_4$— moieties. The term "alkenylene" includes branched, linear and cyclic alkenylene, with linear alkenylene being most preferred.

The term "aryl" is used to define an unsaturated cyclic system which contains a delocalised π-electron system about the ring. Aryl groups may comprise from 4-12 atoms, suitably from 6-8 atoms, most suitably 6 atoms. "Aryl" preferably comprises carbocyclic rings, and is preferably phenyl (—C$_6$H$_5$).

The term "aryl" in the present invention is also used to include aromatic heterocycles—rings in which one or more atoms in the ring (e.g. 1-3 atoms) are N, S, P or O. Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings).

When referring to a linker moiety (e.g. Z, $X_1$, $X_2$, Q, T), the term "aryl" is used to define moieties derived from arenes in which two H atoms have been removed to form a diradical species (i.e. arylene). Examples include 1,2-phenylene, 1,3-phenylene and 1,4-phenylene.

The term "aryl" also includes fused ring systems.

Curing

In the present invention, curing is primarily initiated by exposing the photopolymerizable system containing the polymeric photoinitiators described in the present invention to high energy irradiation, preferably UV light. The photoinitiated process takes place by methods which are known per se, through irradiation with light or UV irradiation in the wavelength range from 100 to 500 nm. Irradiation sources which may be used are sunlight or artificial lamps or lasers. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm), some advantages are obtained with respect to the depth of the curing, provided that the photoinitiator can successfully cure the material at these wavelength. In particular, scattering phenomena are less pronounced at longer wavelength, thus giving a larger penetration depth in the material. Thus, photoinitiators which absorb, and can induce curing, at longer wavelength are of interest. By judicially choosing substituents on the photoinitiator moieties, the absorption spectrum of the polymeric photoinitiator can to some extent be red-shifted, which would then facilitate curing at comparatively greater depths.

Polyurethanes

The polymeric photoinitiators of the present invention are preferably polyurethanes. A polyurethane (PU) is a polymer consisting of a chain of organic units joined by urethane (carbamate) moieties —NH—(C=O)—O—. Polyurethanes are formed by the reaction between one monomer having at least two isocyanate functional groups (—NCO), and another monomer having at least two alcohol (—OH) groups. In their simplest form, due to the nature of the monomers from which they are prepared, polyurethanes comprise alternating A and B monomers (ABABABABA ... ).

Similar polymers are provided based on polyurethanes in which the isocyanate groups are replaced with isothiocyanate (—NCS) groups. —NH—(C=S)—O— moieties are thereby provided.

Polyureas

A polyurea is a polymer consisting of a chain of organic units joined by urea (carbamide) moieties —NH—(C=O)—NH—. Polyureas are typically formed by the reaction between one monomer having at least two isocyanate functional groups (—NCO), and another monomer having at least two amine (—NH$_2$) groups.

Similar polymers in which the amine groups in the monomers are replaced with thiol (—SH) groups are known as polythioureas and include the moiety —NH—(C=O)—S—.

Similarly, the term includes polymers based on ureas in which the isocyanate groups are replaced with isothiocyanate (—NCS) groups. —NH—(C=S)—NH— moieties are thereby provided.

Polyesters

A polyester is a polymer consisting of a chain of organic units joined by ester moieties —(C=O)—O—. Polyesters are typically formed by the reaction between one monomer having at least two activated carboxylic acid functional groups (—COX, where X is, e.g., a chloride or anhydride), and another monomer having at least two alcohol (—OH) groups.

Polycarbonate

A polycarbonate is a polymer consisting of a chain of organic units joined by carbonate moieties —O—(C=O)—O—.

Specific Embodiments of the Invention

The present invention thus provides a polymeric photoinitiator. The polymeric photoinitiator is a co-polymer of at least one monomer (A) with at least one monomer (B). Polymerization is achieved by step-growth co-polymerization of monomers (A) and (B). The physical, chemical and photo-catalytic properties of the polymeric photoinitiator can be varied depending on the nature and relative amounts of the monomers (A) and (B).

Monomer (A) is a photoinitiator monomer (A) of the formula (I):

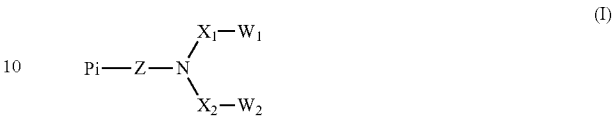

The photoinitiator monomers (A) of the general formula I comprise a photoinitiator moiety, Pi, which provides the photoinitiators with the required response to UV radiation. A photoinitiator moiety is defined as a substance (other than a reactant) which, on absorption of light, generates reactive species (ions or radicals) and initiates one or several chemical reactions or transformations. One preferred property of the photoinitiator moiety is good overlap between the UV light source spectrum and the photoinitiator absorption spectrum. Another desired property is a minor or no overlap between the photoinitiator absorption spectrum and the intrinsic combined absorption spectrum of the other components in the polymer matrix. Good compatibility of the photoinitiator moiety in the matrix consisting of material to be cured is also a property of interest.

The photoinitiator moieties of the invention are efficient in transforming light from the UV or visible light source to reactive radicals which can abstract hydrogen atoms and other labile atoms from polymers and hence effect polymerization and cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Addition of electron donors is not required but may enhance the overall efficiency of cleavable photoinitiator moieties.

Recently, a new class of β-keto ester based photo-initiators has been introduced by M. L Gould, S, Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz. After base-catalyzed Michael addition of the ester to polyfunctional acrylates, a network is formed with a number of quaternary carbon atoms, each with two neighbouring carbonyl groups. Upon UV or visible light excitation, these photoinitiators predominantly cleave by a Norrish type I mechanism and cross-link further without any conventional photo-initiator present, and thick layers may be cured. Such self-initiating systems are within the scope of the photoinitiator moieties of the present invention.

Excited non-cleavable photoinitiator moieties do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones and related ketones such as thioxanthones, xanthones, anthraquinones, fluorenones, dibenzosuberones, benzils, and phenyl ketocoumarins are important examples of non-cleavable photoinitiators, and fall within the definition of photoinitiator moieties according to the present invention. Most amines with a C—H bond in α-position to the nitrogen atom and many thiols will work as electron donors.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photoinitiator moiety; this could make it possible to cure thick layers.

UV self-crosslinkable terpolymers based on acrylonitrile, methyl acrylate and a UV sensitive comonomer, acryloyl benzophenone (ABP), have also been reported (A. K. Naskar et al. Carbon 43 (2005) 1065-1072; T. Mukundan et al. Polymer 47 (2006) 4163-4171). The free radicals generated during UV irradiation of the terpolymer have been shown to enhance crosslinking and cyclization of nitrile units within the polymer.

A blend of several photoinitiator moieties may exhibit synergistic properties, as is e.g. described by J. P. Fouassier: "Excited-State Reactivity in Radical Polymerization Photoinitiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethylbenzophenone], [thioxanthone+methylthiophenyl morpholinoalkyl ketone]. However, many other beneficial combinations may be envisaged. So, in an embodiment of the invention, the photoinitiator moiety Pi includes at least two different types of photoinitiator moieties. Preferably, the absorbance peaks of the different photoinitiator moieties are at different wavelengths, so the total amount of light absorbed by the system increases. The different photoinitiator moieties may be all cleavable, all non-cleavable, or a mixture of cleavable and non-cleavable. Preferably, however, the photoinitiator Pi comprises only one photoinitiator moiety.

Furthermore, it has recently been found that covalently linked 2-hydroxy-1-(4-(2-hydroxyethoxy)phenyl)-2-methylpropan-1-one, which is commercially available with the trade name Irgacure 2959, and benzophenone in the molecule 4-(4-benzoylphenoxy ethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20, 2005, vol. 2, p. 375-81, Vincentz. This shows that different photoinitiator moieties may show significant synergistic effects when they are present in the same oligomer or polymer. Such covalently linked photoinitiator moieties are also within the scope of the present invention.

Photoinitiator moieties (Pi) in Formula (I) may be selected from, but not exclusively restricted to, the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, silanes, maleimides and derivatives thereof. Of these, preferred photoinitiator moieties are selected from benzophenones, thioxanthones, benzilketals and phenyl hydroxyalkyl ketones, such as 2-hydroxy-2-methyl-1-phenylpropan-1-ones.

In particular, Pi may be a benzophenone having the general formula (V):

(V)

wherein $Ar_1$ and $Ar_2$ are independently selected from the same or different optionally substituted aryl, and where Z (which binds to $Ar_2$ as shown by the wavy line) may be present at any position on $Ar_2$. Suitably, $Ar_1$ and $Ar_2$ are the same. Benzophenones are well-studied, commercially-available photoinitiator moieties, and their UV absorption can be tailored according to the substitution pattern of the aryl groups. Preferred substituents on $Ar_1$ and $Ar_2$ are electron-donating groups or atoms such as N, O, S, amines, esters or thiols. Such substituents provide UV absorption at a longer wavelength, meaning that LED lamps can be used as a UV source. LED lamps provide advantages such as low energy consumption and generate less heat; thus the substrate temperature can be controlled more accurately. Judicious selection of functional groups can be used to obtain absorption maxima in a desired wavelength region (e.g. impart charge-transfer within the photoinitiator). The ketones described in the present invention are inherent electron accepting groups, so careful selection of electron-donating groups as substituents on aromatic entities within the photoinitiator can lead to absorption profiles matching the light source best suited for the desired curing application. Mechanistically, the efficiency of photoinitiator moieties relies on their ability to intersystem cross from an electronic excited (singlet) state to a triplet state. Some literature has described that such intersystem crossing is less efficient when a higher degree of charge transfer is present within the system. Thus the absorption profile of a photoinitiator can be controlled to some extent but not without altering the efficiency of radical formation. (see N. J. Turro, *Modern Molecular Photochemistry*, University Science Books: Sausalito, 1991).

The structure in which PI is attached through an alkoxy link to the aromatic ring of the ketonic PI is preferred. The reasons for this preference are that alkoxy substituents confer greater hydrolytic stability at the same time as increasing the absorption in the 383-387 nm band region. An example of this effect is the comparison of the UV spectrum of chloro-thioxanthone which has an absorption at 385 nm with a $E_1^1$ of 159 whereas, its close relative with a propoxy substituent on the aromatic ring, 1-chloro-4-propoxy thioxanthone has an absorption at 387 nm and an $E_1^1$ of 175. This enhanced extinction coefficient of absorption allows for faster curing.

In benzophenones of formula (V) above, both $Ar_1$ and $Ar_2$ may be optionally substituted phenyl, preferably both phenyl, and Z may be present at any position on $Ar_2$. Suitably, however, Z is present at the para-position on $Ar_2$, as this provides the maximum opportunity for electron interaction with the carbonyl group, and hence maximum stabilisation of the radical formed.

Linker, Z

The portion of the photoinitiator monomer (A) of Formula (I) indicated by Z is a linker. The linker Z acts to both bind the photoinitiator moiety to the polymer backbone and simultaneously hold the photoinitiator moiety at a certain distance from the backbone. Linker Z therefore has two ends. At one end, therefore, Z is joined to the photoinitiator moiety; at the other end, Z is joined to the polymer backbone.

The size of the linker Z is selected according to the desired properties of the polymeric photoinitiator. A short linker Z will provide most opportunity for interaction between the amine group N and the photoinitiator moiety. For example, if Z is a bond, the amine group N will be directly bound to the photoinitiator moiety, providing a potential for stabilisation of the photoinitiator moiety in its radical form. On the other hand, a long linker Z will provide freer movement of the photoinitiator moiety in the polymerization process, which also provides advantages. A rigid structure may lower the possibility that radicals formed at one site propagate to polymer chains in the vicinity of the polymeric photoinitiator, whereas a "loose" structure could facilitate dispersion of radical functionalities over a wider area. Suitably, the linker Z has a molecular weight of less than 10000 Da, suitably less than 5000 Da, most suitably less than 1000 Da. The linker Z preferably comprises no more than 50 atoms, preferably no more than 30 atoms.

In the photoinitiator monomers (A) of Formula (I) above, Z is a linker moiety. Z may be selected from a single bond, optionally substituted $C_1$-$C_{12}$ alkylene, optionally substituted $C_1$-$C_{12}$ alkenylene, —O—, —S—, —$NR^1$—, —C(=O)—, —C(=$NR^1$)—, —$SO_2$—, —P(=O)($OR^1$)—, optionally substituted heterocyclyl, optionally substituted aryl, —[O—($C_1$-$C_{12}$ alkylene)]$_n$-, —[$NHR^1$—($C_1$-$C_{12}$ alkylene)]$_n$, —[S—($C_1$-$C_{12}$ alkylene)]$_n$-, and combinations thereof, wherein Fe is H or optionally substituted $C_1$-$C_{12}$ alkyl and n is an integer from 1-20.

Z may be selected from a single bond, optionally substituted $C_1$-$C_{12}$ alkylene, optionally substituted $C_1$-$C_{12}$ alkenylene, —O—, —S—, —$NR^1$—, —C(=O)—, —C(=$NR^1$)—, optionally substituted heterocyclyl, optionally substituted aryl, —[O—($C_1$-$C_{12}$ alkylene)]$_n$-, —[$NHR^1$—($C_1$-$C_{12}$ alkylene)]$_n$, —[S—($C_1$-$C_{12}$ alkylene)]$_n$-, and combinations thereof, wherein $R^1$ is H or optionally substituted $C_1$-$C_{12}$ alkyl and n is an integer from 1-20.

Suitably, n is an integer from 1-10, more suitably from 1-5, such as e.g. 1, 2, 3, 4 or 5.

$R^1$ may be H. $R^1$ may also be optionally substituted $C_1$-$C_6$ alkyl, such as e.g. methyl, ethyl, propyl, butyl, pentyl or hexyl. $R^1$ may be straight-chain, branched or cyclic alkyl.

In that Z may comprise a combination of the above-mentioned groups, the invention encompasses photoinitiator monomers (A) in which Z is made up of two or more of the above-mentioned groups in series, e.g.

—O—($C_1$-$C_{12}$ alkylene)-
—($C_1$-$C_{12}$ alkylene)-O—($C_1$-$C_{12}$ alkylene)-
—O—($C_1$-$C_{12}$ alkylene)-O—($C_1$-$C_{12}$ alkylene)-
—O—($C_1$-$C_{12}$ alkylene)-O-(aryl)-
—$NR^1$—($C_1$-$C_{12}$ alkylene)-
—($C_1$-$C_{12}$ alkylene)-$NR^1$—($C_1$-$C_{12}$ alkylene)-
—$NR^1$—($C_1$-$C_{12}$ alkylene)-$NR^1$—($C_1$-$C_{12}$ alkylene)-
—$NR^1$—($C_1$-$C_{12}$ alkylene)-O—($C_1$-$C_{12}$ alkylene)-
—O—($C_1$-$C_{12}$ alkylene)-$NR^1$—($C_1$-$C_{12}$ alkylene)-
—C(=O)—O—($C_1$-$C_{12}$ alkylene)-
—C(=O)—$NR^1$—($C_1$-$C_{12}$ alkylene)-
—O—C(=O)—($C_1$-$C_{12}$ alkylene)-
—N—C(=O)—($C_1$-$C_{12}$ alkylene)-
—O-aryl-
—($C_1$-$C_{12}$ alkylene)-C(=O)—$NR^1$—C(=O)—($C_1$-$C_{12}$ alkylene)-.

In all of the above, the —($C_1$-$C_{12}$ alkylene)- and -aryl- groups may be substituted or unsubstituted. Other chemically-feasible structures for Z can be determined by the person skilled in the art.

Suitably, Z is selected from a single bond, optionally substituted $C_1$-$C_{12}$ alkylene, optionally substituted $C_1$-$C_{12}$ alkenylene, —O—, —S—, —$NR^1$—, —[O—($C_1$-$C_{12}$ alkylene)]$_n$-, and combinations thereof, wherein Fe is H or optionally substituted $C_1$-$C_{12}$ alkyl and n is an integer from 1-20. Z may be selected from a bond, optionally substituted $C_1$-$C_{12}$ alkylene, optionally substituted $C_1$-$C_{12}$ alkenylene, —O—, —S—, —$NR^1$—, and —[O—($C_1$-$C_{12}$ alkylene)]$_n$-, wherein $R^1$ is H or optionally substituted $C_1$-$C_{12}$ alkyl and n is an integer from 1-20. Z may also be selected from optionally substituted $C_1$-$C_{12}$ alkylene, preferably optionally substituted $C_1$-$C_6$ alkylene.

Photoinitiator monomers (A) of Formula (I) in which Z comprises an electron-donating group adjacent Pi are advantageous, as this provides opportunities to tailor the UV absorption of the photoinitiator moiety. Accordingly, Z may also be selected from optionally substituted —O—($C_1$-$C_{12}$ alkylene)-, preferably optionally substituted —O—($C_1$-$C_6$ alkylene)-, optionally substituted —S—($C_1$-$C_{12}$ alkylene)-, preferably optionally substituted —S—($C_1$-$C_6$ alkylene)-, and optionally substituted —$NR^1$—($C_1$-$C_{12}$ alkylene)-, preferably optionally substituted —$NR^1$—($C_1$-$C_6$ alkylene)-, wherein $R^1$ is H or optionally substituted $C_1$-$C_{12}$ alkyl. Z may even be selected from optionally substituted —O—($C_1$-$C_{12}$ alkylene)-, preferably optionally substituted —O—($C_1$-$C_6$ alkylene)-.

Most preferably, Z is selected from a bond, optionally substituted $C_1$-$C_6$ alkylene and optionally substituted —O—($C_1$-$C_6$ alkylene)-.

$X_1$ and $X_2$

The groups $X_1$ and $X_2$ of the photoinitiator monomer (A) serve to connect the amine N with the end groups $W_1$ and $W_2$. The size and form of these groups can be varied to adjust the properties of the polyurethane polymer.

$X_1$ and $X_2$ may be the same or different, and are preferably the same, for ease of chemical synthesis. $X_1$ and $X_2$ may be independently selected from optionally substituted $C_1$-$C_{12}$ alkylene, optionally substituted $C_1$-$C_{12}$ alkenylene, —O—, —S—, —$NR^2$—, —C(=O)—, —C(=$NR^2$)—, —Si($R^2$)$_2$—O—, optionally substituted heterocyclyl, optionally substituted aryl, and combinations thereof, wherein $R^2$ is H or optionally substituted $C_1$-$C_{12}$ alkyl. In that $X_1$ and $X_2$ may comprise combinations of the above-mentioned groups, the invention encompasses photoinitiators in which $X_1$ and $X_2$ are made up of two or more of the above-mentioned groups in series.

Suitably, $X_1$ and $X_2$ are independently selected from optionally substituted $C_1$-$C_{12}$ alkylene, optionally substituted $C_1$-$C_{12}$ alkenylene, —O—, —S—, —$NR^2$—, —C(=O)—, —C(=$NR^2$)—, optionally substituted heterocyclyl, optionally substituted aryl, wherein $R^2$ is H or optionally substituted $C_1$-$C_{12}$ alkyl.

$R^2$ may be H. $R^2$ may also be optionally substituted $C_1$-$C_6$ alkyl, such as e.g. methyl, ethyl, propyl, butyl, pentyl or hexyl. $R^2$ may be straight-chain, branched or cyclic alkyl.

$X_1$ and $X_2$ may be linked to one another or to Z to form one or more ring structures.

$X_1$ and $X_2$ may independently be selected from optionally substituted $C_1$-$C_{12}$ alkylene, —O—, —S—, —$NR^2$—, wherein $R^2$ is H or optionally substituted $C_1$-$C_{12}$ alkyl, and combinations thereof. $X_1$ and $X_2$ may be linked to one another to form one or more ring structures. Additionally, $X_1$ and $X_2$ may independently be selected from optionally substituted $C_1$-$C_{12}$ alkylene, preferably optionally substituted $C_1$-$C_6$ alkylene.

Tertiary Amine, N

In the photoinitiator monomers (A) described by Formula (I), N represents a tertiary amine (i.e. a nitrogen atom bound directly to three carbon atoms, in which the carbon atoms are saturated alkyl or aryl carbon atoms).

The N atom in the photoinitiator monomers (A) of Formula (I) has a number of functions. Firstly, it provides the appropriate branching of the molecule, so that the photoinitiator moieties are pendant from the polyurethane backbone.

Secondly, the N atom in the photoinitiator monomers (A) of Formula (I)—being a tertiary amine—is basic. Suitably, the N atom has a $pK_b$ of less than 13, preferably a $pK_b$ less than 6. The amine N atom is therefore able to partially or completely replace the amine catalysts which are typically used in polyurethane (and similar) polymerization reactions (e.g. 1,4-diazabicyclo[2.2.2]octane (DABCO), dimethylcyclohexylamine (DMCHA) and dimethylethanolamine (DMEA)). In this way, the use of any low molecular weight tertiary amine catalysts in the polymerization between monomers (A) and (B) can be reduced or completely avoided.

In addition, the tertiary amine in the structure when irradiated with UV can have a proton abstracted by the aromatic ketone part of the structure (either intramolecularly or intermolecularly) from the carbon atoms adjacent to the amino nitrogen. This will give rise to an active radical capable of initiating polymerization or cross-linking.

Z, $X_1$ and $X_2$ are selected such that N is a tertiary amine (i.e. so that the atom adjacent N is a saturated carbon atom, or an aryl carbon atom) so that the basic properties of N are preserved. Preferably, at least two of the groups Z, $X_1$ and $X_2$ in the tertiary amine are alkyl.

End Groups, $W_1$, $W_2$

The end groups $W_1$ and $W_2$ in the photoinitiator monomers (A) of Formula (I) allow the photoinitiator monomer (A) to be incorporated into a growing polymer chain. $W_1$ and $W_2$ are therefore selected from those functional groups which are reactive, and which are able to bond to other monomers to thus form polymers such as polyurethane. As such, $W_1$ and $W_2$ are independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups.

Secondary amines may have the formula —$NHR^3$, where $R^3$ is optionally substituted $C_1$-$C_{12}$ alkyl.

Suitably, $W_1$ and $W_2$ are independently selected from alcohol, primary amine, secondary amine or thiol groups.

Care should be taken when selecting suitable $X_1$ and $X_2$ groups, such that $W_1$ and $W_2$ fulfil these criteria. For example, $X_1$ and $X_2$ may independently be selected from optionally substituted $C_1$-$C_{12}$ alkylene, when $W_1$ and $W_2$ are —OH.

$R^3$ and $R^4$ may independently be optionally substituted $C_1$-$C_6$ alkyl, such as e.g. methyl, ethyl, propyl, butyl, pentyl or hexyl. $R^3$ and $R^4$ may be straight-chain, branched or cyclic alkyl.

$W_1$ and $W_2$ are selected according to the design of the polymer. If desired, $W_1$ and $W_2$ may be different end groups. It is preferable for ease of synthesis of the photoinitiator monomer (A), however, that $W_1$ and $W_2$ are the same.

In that only two end groups $W_1$ and $W_2$ are present, the photoinitiator monomer (A) does not promote branching of the polymeric photoinitiator. Instead, the photoinitiator monomers (A) of Formula (I) are incorporated partly into the backbone of the polymeric photoinitiators, while the photoinitiator moieties Pi are pendant from the chain via linker Z.

Further Structures for Photoinitiator Monomer (A)

A sub-structure which describes photoinitiator monomers (A) of Formula I has the general formula (Ia)

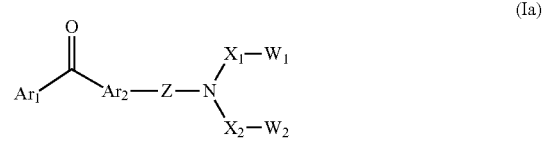

wherein $Ar_1$, $Ar_2$, Z, N, $X_1$, $X_2$, $W_1$ and $W_2$ are as defined above and where Z may be present at any position on $Ar_2$. In the photoinitiator monomers (A) of Formula Ia, $Ar_1$ and $Ar_2$ may both be optionally substituted phenyl, and are preferably both phenyl. Suitably, Z is present at the para-position on $Ar_2$.

Another sub-structure which describes photoinitiator monomers (A) of Formula (I) has the general formula (Ib):

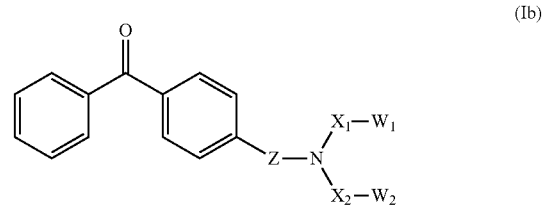

in which Z, N, $X_1$, $X_2$, $W_1$ and $W_2$, and preferred options for these groups, are as defined above.

Another sub-structure which describes photoinitiator monomers (A) of Formula (I) has the general formula (Ic):

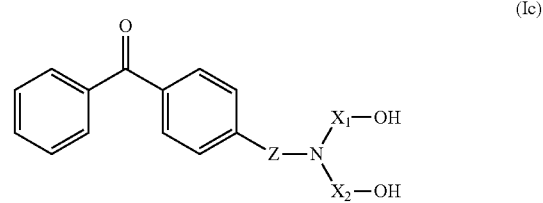

wherein Z, N, $X_1$, and $X_2$, and preferred options for these groups, are as defined above.

Suitable photoinitiator monomers (A) according to the invention include:
{4-[bis(2-hydroxyethyl)amino]phenyl}(phenyl)methanone
(4-{[bis(2-hydroxyethyl)amino]methyl}phenyl)(phenyl) methanone

[4-({2-[bis(2-hydroxyethyl)amino]ethyl}sulfanyl)phenyl](phenyl)methanone
(4-{3-[bis(2-hydroxyethyl)amino]propoxy}phenyl)(phenyl)methanone
{4-[bis(2-hydroxypropyl)amino]phenyl}(phenyl)methanone
N,N-bis(2-hydroxyethyl)-2-(phenylcarbonyl)benzamide
N,N-bis(2-hydroxypropyl)-2-(phenylcarbonyl)benzamide
3,4-dihydroxy-1-[4-(phenylcarbonyl)phenyl]pyrrolidine-2,5-dione
N,N-bis[2-(methylamino)ethyl]-4-(phenylcarbonyl)benzamide
(4-{[bis(2-hydroxyethyl)amino]methyl}phenyl)[4-(phenylsulfanyl)phenyl]methanone
4-{3-[bis(2-hydroxyethyl)amino]propoxy}-1-chloro-9H-thioxanthen-9-one
4-[{2-[bis(2-hydroxyethyl)amino]ethyl}(methyl)amino]-1-chloro-9H-thioxanthen-9-one
2-[bis(2-hydroxyethyl)amino]ethyl [(9-oxo-9H-thioxanthen-2-yl)oxy]acetate
1-[bis(2-hydroxyethyl)amino]-4-propoxy-9H-thioxanthen-9-one
2-[(1-chloro-9-oxo-9H-thioxanthen-4-yl)oxy]-N,N-bis(2-hydroxyethyl)acetamide
1-{4-[bis(2-hydroxyethyl)amino]phenyl}-2-hydroxy-2-methylpropan-1-one
1-(4-{2-[bis(2-hydroxyethyl)amino]ethoxy}phenyl)-2-hydroxy-2-methylpropan-1-one
2-methyl-2-(morpholin-4-yl)-1-(4-{[bis(2-hydroxyethyl)amino]methyl}phenyl)propan-1-one
(3',5'-diisocyanatobiphenyl-4-yl)(phenyl)methanone.

Photoinitiators according to the invention of particular interest are
{4-[bis(2-hydroxyethyl)amino]phenyl}(phenyl)methanone
(4-{[bis(2-hydroxyethyl)amino]methyl}phenyl)(phenyl)methanone
(4-{3-[bis(2-hydroxyethyl)amino]propoxy}phenyl)(phenyl)methanone
{4-[bis(2-hydroxypropyl)amino]phenyl}(phenyl)methanone
N,N-bis(2-hydroxyethyl)-2-(phenylcarbonyl)benzamide
4-{3-[bis(2-hydroxyethyl)amino]propoxy}-1-chloro-9H-thioxanthen-9-one
2-[bis(2-hydroxyethyl)amino]ethyl [(9-oxo-9H-thioxanthen-2-yl)oxy]acetate
2-[(1-chloro-9-oxo-9H-thioxanthen-4-yl)oxy]-N,N-bis(2-hydroxyethyl)acetamide
1-{4-[bis(2-hydroxyethyl)amino]phenyl}-2-hydroxy-2-methylpropan-1-one.

Routes Ia, Ib and Ic are nucleophilic substitution, or carbonyl group transformation (i.e. nitrogen acylation). LG depicts a leaving group (preferably Cl, Br, I, OMs, OTs, OTf). The base used is preferably amine, alkali metal alkoxide, hydroxide or carbonate.

Route II is a nucleophilic aromatic substitution. LG depicts a leaving group (preferably F, Cl). The base is preferably amine, alkali metal alkoxide, hydroxide or carbonate.

Route III is a cross-coupling reaction. LG depicts a leaving group (preferably Cl, Br, I, OMs, OTs, OTf). M depicts a nucleophilic organometallic substituent (preferably $R_2Al$—, $RZn$—, $R_3Sn$—, $RMg$—, $Li$—, $(RO)_2B$—). The transition metal catalyst is a salt or transition metal complex (preferably containing Pd, Pt, Ni, Ir, Rh, Ru, Cu, Fe).

Routes IVa and IVb are Friedel-Crafts acylations. The Lewis acid may be preferably $BF_3$, $BCl_3$, $AlCl_3$, $FeCl_3$ or $SnCl_4$.

Route V may be a reaction of an aryl organometallic reagent with an acyl derivative. M depicts a nucleophilic organometallic substituent (preferably $RMg$—, $RZn$—, $RCd$— or $R_3Sn$—).

Route VI is oxidation of a diarylmethanol. Preferable oxidants include manganese, ruthenium, chromium reagents and Swern oxidation.

Route VII may be nitrogen alkylation or acylation. Suitably, one or both reagents $LG-X_1$—$W_1$ and $LG-X_2$—$W_2$ may contain an epoxide (aziridine) which is opened by the nucleophilic nitrogen to reveal a reactive hydroxy (amino) end group.

The other component of the polymeric photoinitiator is at least one monomer (B). Monomer (B) comprises at least two functional groups $W_3$ and $W_4$, said $W_3$ and $W_4$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups.

Monomer (B) may have a structure of formula II:

$$W_3\text{-}Q\text{-}W_4 \quad \text{(II)}$$

wherein $W_3$ and $W_4$ are defined as in claim 1 and wherein Q is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, optionally substituted biaryl, —[O—($C_1$-$C_{12}$ alkylene)]$_m$—, —[S—($C_1$-$C_{12}$ alkylene)]$_m$—, where m is an integer from 1-1000 and combinations thereof. Q could also comprise one of the photoinitiator moieties (Pi) set out above.

Q may be selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, and optionally substituted biaryl. Q may be selected from the group consisting of optionally substituted aryl and optionally substituted biaryl.

Suitably, $W_3$ and $W_4$ are independently selected from isocyanate and thioisocyanate groups. Typically, $W_3$ and $W_4$ are the same functional groups.

In particular embodiments, monomer (B) is a polyisocyanate, preferably a diisocyanate. Suitable polyisocyanates have an average of about two or more isocyanate groups, preferably an average of about two to about four isocyanate groups and include aliphatic, cycloaliphatic, araliphatic and aromatic polyisocyanates, used alone or in mixtures of two or more. Diisocyanates are preferred.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate and the like. Polyisocyanates having fewer than 5 carbon atoms can be used but are less preferred because of their high volatility and toxicity. Preferred aliphatic polyisocyanates include hexamethylene-1,6-diisocyanate, 2,2,4-trimethyl-hexamethylenediisocyanate and 2,4,4-trimethyl-hexamethylene diisocyanate.

Specific examples of suitable cycloaliphatic polyisocyanates include dicyclohexylmethane diisocyanate, isophorone diisocyanate, 1,4-cyclohexane diisocyanate, 1,3-bis-(isocyanatomethyl)cyclohexane and the like. Preferred cycloaliphatic polyisocyanates include dicyclohexylmethane diisocyanate and isophorone diisocyanate.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate.

Examples of suitable aromatic polyisocyanates include 4,4'-diphenylmethylene diisocyanate, toluene diisocyanate, their isomers, naphthalene diisocyanate and the like. A preferred aromatic polyisocyanate is toluene diisocyanate.

Monomer (B) may be selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI) and 1,3-bis(isocyanato-methyl)cyclohexane (HXDI).

Importantly, $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety. Suitably, $W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety. Of most interest is the situation in which $W_1$ reacts with $W_3$ to form a urethane, or thiourethane moiety, and $W_2$ reacts with $W_4$ to form a urethane or thiourethane moiety.

Given a particular $W_1$ or $W_2$, the skilled person will be able to select the appropriate $W_3$ or $W_4$ to provide the polymeric photoinitiators of the invention.

Preferably, the polymeric photoinitiator is a polyurethane photoinitiator. In this case, $W_1$ and $W_2$ are selected to be alcohol functional groups, and $W_3$ and $W_4$ are selected as isocyanate groups to provide urethane moieties when monomer (A) reacts with monomer (B). A polyurethane photoinitiator will thus be formed. The reverse arrangement ($W_1$ and $W_2$ are isocyanate functional groups, while $W_3$ and $W_4$ are alcohol groups) will also provide a polyurethane.

Similarly, if $W_1$ and $W_2$ are thiol functional groups, selection of $W_3$ and $W_4$ as isocyanate groups will provide thiourethane moieties when monomer (A) reacts with monomer (B). The reverse arrangement is also possible.

To form urea moieties from $W_1$-$W_4$, it is possible to select $W_1$ and $W_2$ as amine functional groups and $W_3$ and $W_4$ as isocyanate functional groups. Polyurea photoinitiators will thus be formed. The reverse situation is also possible ($W_1$ and $W_2$ are isocyanate functional groups, while $W_3$ and $W_4$ are amine functional groups).

Suitably, $W_3$ and $W_4$ are the same functional groups, as are $W_1$ and $W_2$. However, it is possible that $W_1$ and $W_2$ are different, as long as $W_3$ and $W_4$ are selected such that a polymer may be formed.

More than one type of monomer (A) and more than one type of monomer (B) may be used in the polymeric photoinitiators of the invention. As well as the regular structure . . . ABABABAB . . . , the polymeric photoinitiators may therefore also have a structure which incorporates variations of monomers A and B, e.g. . . . A'BABA'B'A'B'A'BABA'B' . . . .

One or more additional monomers (C) may also be present in the polymeric photoinitiators of the invention. Each of said one or more additional monomers (C) comprises at least two functional groups $W_5$ and $W_6$, said $W_5$ and $W_6$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups, wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety. Suitably, $W_5$ reacts with $W_1$ or $W_3$ to form a urethane, thiourethane, urea, thiourea, ester or amide moiety, and $W_6$ reacts with $W_2$ or $W_4$ to form a urethane, thiourethane, urea, thiourea, ester, or amide moiety.

Depending on the choice of $W_5$ and $W_6$, and the relative amounts of monomers (A), (B) and (C), the polymeric photoinitiator may have a variety of repeating structures such as e.g.:

. . . ABABABABCBABABCBAB . . . (if $W_5$ and $W_6$ react with $W_3$ and $W_4$)

. . . ABABACACABABABACAC . . . (if $W_5$ and $W_6$ react with $W_1$ and $W_2$)

Monomer (C) may have a structure of formula III:

$$W_5\text{-}T\text{-}W_6 \quad (III)$$

wherein $W_5$ and $W_6$ are defined above, and wherein T is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, optionally substituted biaryl, —[O—($C_1$-$C_{12}$ alkylene)]$_n$-, —[S—($C_1$-$C_{12}$ alkylene)]$_n$-, where n is an integer from 1-1000, and combinations thereof. T may be selected from the group consisting of —[O—($C_1$-$C_{12}$ alkylene)]$_m$—, —[S—($C_1$-$C_{12}$ alkylene)]$_m$—, where m is an integer from 1-1000.

Suitably, $W_5$ and $W_6$ are independently selected from alcohol, primary amine, secondary amine, or thiol functional groups, preferably alcohol functional groups. Typically, $W_5$ and $W_6$ are the same functional groups.

Monomer (C) may be used to determine the physical properties of the polymeric photoinitiator. Monomer (C) may e.g. promote water solubility. Suitably, monomer (C) may be a macromonomer, i.e. a polymer or oligomer that has a functional group that can take part in further polymerization. As such, monomer (C) may be selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton) diol, poly(1,6-hexanediol carbonate) and poly(ethylene terephthalate) diol. Monomer (C) may also comprise diols of other poly(C1-C6) alkylene oxides.

Monomer (C) could also be a low molecular weight monomer, such as a C1-C10 diol, e.g. 1,2-ethanediol, 1,3-propanediol or 1,4-butanediol.

The weight ratio of monomers (A):(B) is suitably 1:99-99:1, preferably 1:99-50:50. The weight ratio of monomers (A):(C) is suitably 1:99-99:1, preferably 1:99-50:50. The weight of the photoinitiator monomer (A) used to prepare polymeric photoinitiators may be between 0.1% and 99% of the total mass of other monomers, suitably between 0.2% and 10%, most suitably 0.5% to 5%.

Suitably, the polymeric photoinitiator has a molecular weight of more than 1 kDa, suitably between 10 kDa and 1000 kDa, most suitably between 20 kDa and 100 kDa.

In the polymeric photoinitiator, the photoinitiator moiety Pi is pendant from the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

The invention also relates to a method for producing a polymeric photoinitiator, said method comprising step-growth co-polymerization of at least one monomer (A) with at least one monomer (B), wherein (A) and (B) have the structures described above. Preferably the polymeric photoinitiator is a polyurethane photoinitiator. The co-polymerization reaction may additionally comprise one or more additional monomers (C), having the structure described above. Co-polymerization of monomers (A) and (B) may take place using any suitable reaction conditions, catalysts or reagents known to the skilled person. For instance, amines such as DABCO are known to catalyse polyurethane formation.

The polymeric photoinitiator may also include one or more branched monomers, comprising 3 or more functional groups which react with $W_1$-$W_4$ of monomers A and B. Cross-linking in the polymer structure is therefore achieved.

The polymeric photoinitiators (e.g. polyurethane photoinitiators) of the present invention form radical species upon exposure to radiation and/or heat. Application of radiation (as described in the section above entitled "Curing") excites the photoinitiator moiety, Pi, which then extracts protons from neighbouring functionalities, forming reactive radicals.

If the polymeric photoinitiator is the only component when irradiated, it will cross-link with itself, providing a cured polymer. The invention thus provides a method of cross-linking the polymeric photoinitiator of the invention, said method comprising exposing the polymeric photoinitiator as described herein to UV radiation and/or heat.

If the polymeric photoinitiator of the invention is mixed with monomers which can undergo radical polymerization (e.g. alkene monomers or acrylate monomers), rapid curing (=polymerization and cross-linking) of such monomers can occur. The present invention thus provides the use of a polymeric photoinitiator as described herein as a photoinitiator of radical polymerization.

It has been found that the polymeric photoinitiators of the present invention act to cure polymer matrices, at least as effectively, if not more effectively than known photoinitiators.

Example 1

4-{3-[bis(2-hydroxyethyl)amino]propoxy}benzophenone

RELEVANT LITERATURE: J. Med. Chem. 2001, 3810-3820; J. Med. Chem. 1998, 3976-3986; J. Med. Chem. 1989, 105-118.

A 1000 mL three-neck flask was charged with 4-hydroxybenzophenone (50.00 g; 252.2 mmol), 1-bromo-3-chloropropane (79.41 g; 504.4 mmol) and 2-butanone (500 mL). After flushing with nitrogen, anhydrous potassium carbonate (104.6 g; 756.5 mmol) was added and the reaction mixture was stirred at reflux for 24 h. Full consumption of the starting 4-hydroxybenzophenone was confirmed by TLC. The reaction mixture was filtered, the filtrate evaporated, the oily residue dissolved in dichloromethane (300 mL) and extracted with water (3×100 mL). The organic phase was separated, evaporated, and the unreacted 1-bromo-3-chloropropane was removed by heating to 70° C. in vacuo. The residue was dissolved in 2-butanone (500 mL) and sodium iodide (45.36 g; 302.6 mmol) was added. The reaction mixture was refluxed for 6 h. The reaction mixture was filtered, the filtrate evaporated, the oily residue dissolved in dichloromethane (300 mL) and extracted with water (3×100 mL). The organic phase was separated, evaporated, the light brown oily residue dried in vacuo to give crude 4-(3-iodopropoxy)benzophenone (light brown solid; 83.2 g).

To the crude product from the previous step (83.2 g; 227.2 mmol) was added toluene (100 mL), 2-propanol (200 mL) and diethanolamine (179.2 g; 1.704 mol). The reaction mixture was refluxed (110° C.) for 16 h. After evaporation of ethanol and toluene, water (2000 mL) was added to precipitate the oily product. The emulsion obtained was thoroughly extracted with diethyl ether (6×300 mL). The aqueous phase was discarded and the organic phase was extracted with hydrochloric acid (6M, 3×200 mL). The pH of the strongly acidic aqueous phase was adjusted to 12-13 by slow addition of 35% aq. ammonia to reprecipitate the product. The aqueous phase was reextracted with dichloromethane (3×300 mL), the organic phase dried (MgSO$_4$), evaporated and the light brown oily product dried in vacuo.

This provides 4-{3-[bis(2-hydroxyethyl)amino]propoxy}benzophenone (57.7 g; 74% yield).

$^1$H-NMR (400 MHz, chloroform-d): 7.80 (d, J=8.8 Hz, 2H), 7.73 (d, J=8.3 Hz, 2H), 7.55 (m, 1H), 7.46 (t, J=7.8 Hz, 2H), 6.95 (d, J=8.8 Hz, 2H), 4.12 (t, J=6.0 Hz, 2H), 3.62 (t, J=5.3 Hz, 4H), 2.87 (bs, 2H), 2.75 (t, J=6.9 Hz, 2H), 2.67 (t, J=5.3 Hz, 4H), 1.96 (apparent quintet, J=6.4 Hz, 2H). UV (MeCN): $\lambda_{max}$=286 nm.

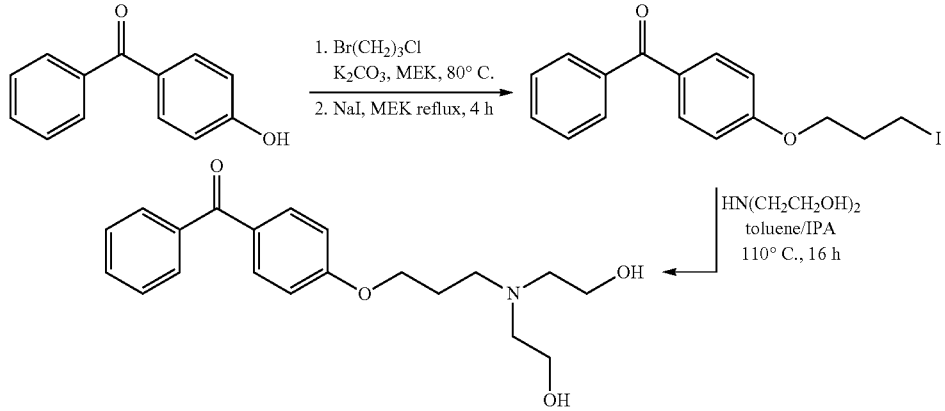

Large Scale Prep:

A 5000 mL three-neck flask was charged with 4-hydroxybenzophenone (800.0 g; 4.036 mol), 1-bromo-3-chloropropane (832.5 g; 5.288 mol) and 2-butanone (3300 mL). Anhydrous potassium carbonate (673.6 g; 4.874 mol) was added and the reaction mixture was stirred at reflux for 100 h. Full consumption of the starting 4-hydroxybenzophenone was confirmed by HPLC. The reaction mixture was filtered, the inorganic solids were washed with 2-butanone (3×100 mL). The filtrate was evaporated, and the unreacted 1-bromo-3-chloropropane was removed by heating to 70° C. in vacuo. The residue was dissolved in acetonitrile (2000 mL) and sodium iodide (650.0 g; 4.337 mol) was added. The reaction mixture was refluxed for 8 h. The reaction mixture was filtered to give a solution of crude 4-(3-iodopropoxy)benzophenone.

The crude acetonitrile solution from the previous stage was charged over a period of 6 hours into neat diethanolamine (2800 g; 26.63 mol) heated to 70° C. After the end of the feed, the reaction mixture heated to reflux for a further 2 h. Full consumption of the starting material was confirmed by TLC. The reaction mixture was poured into water (10 L) and the resulting suspension extracted with dichloromethane (3×1500 mL). The organic phase was separated and extracted with 1 M aq. HCl (4000 mL). The organic phase was discarded and the aqueous phase was made strongly alkaline (pH 12) by slow addition of 50% aq. NaOH. The resulting suspension was extracted with dichloromethane (3×1000 mL). The organic layer was dried (MgSO₄), filtered and evaporated. The light brown oil was dried in high vacuo at 80° C. This provides 4-{3-[bis(2-hydroxyethyl)amino]propoxy}benzophenone (1180 g; 85.1% yield over 3 steps).

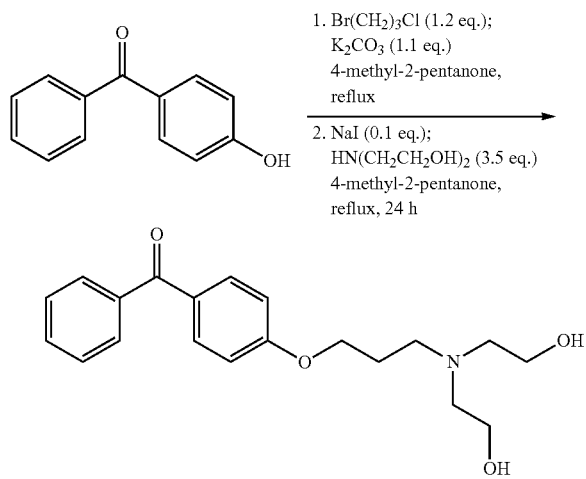

Procedure:

A 500 mL three-neck flask was charged with 4-hydroxybenzophenone (80.00 g; 0.4036 mol), 1-bromo-3-chloropropane (76.25 g; 0.4843 mol) and 4-methyl-2-pentanone (330 mL). Anhydrous potassium carbonate (61.36 g; 0.4440 mol) was added and the reaction mixture was stirred at reflux (120° C.) for 4 h. HPLC analysis shows that the reaction mixture contains 90.0% 4-(3-chloropropoxy)benzophenone; 7.0% 1,3-bis(4-benzoylphenoxy)propane and 0.8% 4-hydroxybenzophenone. The reaction mixture was filtered hot and the inorganic solids were washed with 4-methyl-2-pentanone (100 mL). The filtrate was charged into a mixture of diethanolamine (148.5 g; 1.412 mol), sodium iodide (6.05 g; 0.0404 mol) and 4-methyl-2-pentanone (150 mL). The reaction mixture heated to reflux (122° C.) for 24 h. The reaction mixture was cooled to room temperature and extracted with water (500 mL). The organic phase was extracted with 1 M HCl (500 mL) at 70° C. to prevent crystallisation of the 1,3-bis(4-benzoylphenoxy)propane byproduct. The aqueous phase was separated, cooled to room temperature and taken to pH 12 with 50% aqueous NaOH. The resulting emulsion was extracted with 4-methyl-2-pentanone (3×200 mL). The organic phase was separated, dried (MgSO₄), filtered and the solvent removed in vacuo. This provides 4-{3-[bis(2-hydroxyethyl)amino]propoxy}benzophenone (123.2 g; 89% yield over 3 steps).

Example 2

4-{[bis(2-hydroxyethyl)amino]methyl}-benzophenone

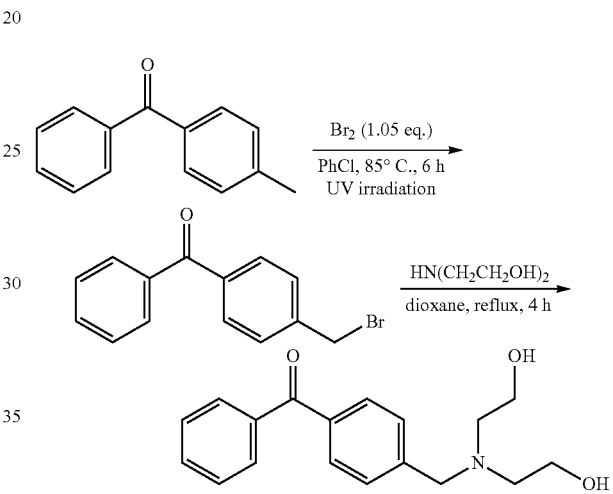

RELEVANT LITERATURE: Tetrahedron 2009, 4429-4439.

A 5000 mL three-neck flask was charged with 4-methylbenzophenone (1100 g; 5.605 mol). The starting material was dissolved in chlorobenzene (2500 mL) and the reaction mixture warmed to 75° C. A solution of bromine (302 mL; 5.886 mol) in chlorobenzene (500 mL) was added to the reaction vessel in 100 mL portions over 6 hours. The reaction temperature was maintained at 85° C. and the reaction vessel was irradiated with a 240 W incandescent bulb. Hydrogen bromide gas evolved during the reaction was neutralised with an aqueous KOH scrubber system. After complete disappearance of orange coloration, the reaction mixture was cooled to ambient temperature and all volatiles removed in vacuo. The residue was dried under oil pump vacuum for 4 h at 60° C. Pale yellow-orange solid was obtained upon cooling (1500 g). 1H-NMR indicates that the crude product contains 20% 4-methylbenzophenone, 71% 4-(bromomethyl)benzophenone and 9% 4-(dibromomethyl)benzophenone. The crude product was used directly in the next step.

A 10000 mL three-neck flask was charged with diethanolamine (4400 g; 41.85 mol). After warming to 90° C., a slurry of crude material from the previous step (1500 g) in dioxane (2000 mL) was added to the oily reaction mixture in 6 portions over a period of 2 hours. After the addition was complete, the reaction was taken to gentle reflux (100° C.) and heated for a further 2 hours. Complete conversion of 4-(bromomethyl)benzophenone was confirmed by TLC. Dioxane was removed from the reaction by evaporation under reduced pressure. The oily orange residue was poured into water (20 L) and extracted with ethyl acetate (3×1500 mL). The aqueous phase was discarded and the organic phase was extracted with hydrochloric acid (1.2M, 3×1000 mL). The pH of the strongly acidic aqueous phase was adjusted to 12-13 by slow addition of 50% aq. NaOH to reprecipitate the product. Most of the product separated out as an orange oil. The residual aqueous phase was reextracted with dichloromethane (3×500 mL), combined organic phases were dried ($Na_2SO_4$), volatiles were evaporated under reduced pressure and the light brown oily product dried under oil pump vacuum (6 h, 60° C.).

This provides 4-{[bis(2-hydroxyethyl)amino]methyl}benzophenone (1170 g; 70.0% yield over 2 steps).

1H-NMR (400 MHz, chloroform-d): 7.80-7.75 (m, 4H), 7.58 (tt, J=7.4, 1.4 Hz, 1H), 7.50-7.44 (m, 4H), 3.79 (s, 2H), 3.65 (t, J=5.4 Hz, 4H), 2.74 (t, J=5.4 Hz, 4H), 2.59 (bs, 2H). UV (MeCN): $\lambda_{max}$=255 nm.

Example 3

{4-[bis(2-hydroxyethyl)amino]phenyl}(phenyl)methanone

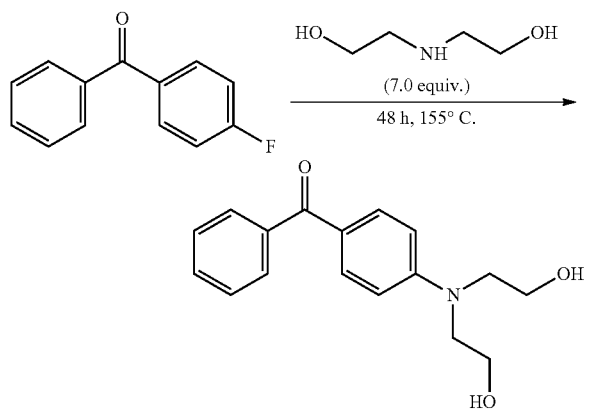

RELEVANT LITERATURE: *J. Phys. Org. Chem.* 2001, 14, 247-255; *J. Med. Chem.* 1991, 34, 1552-1560.

A 100 mL two-neck flask was charged with 4-fluorobenzophenone (15.0 g; 74.9 mmol) and diethanolamine (55.1 g; 524 mmol). The flask was flushed with nitrogen, fitted with a reflux condenser and heated to 155° C. for 48 h under a gentle stream of nitrogen. Complete conversion of the starting 4-fluorobenzophenone was confirmed by TLC. After cooling to ambient temperature, the dark viscous reaction mixture was poured into water (2000 mL). The resulting suspension was thoroughly extracted with diethyl ether (6×250 mL). The aqueous phase was discarded and the organic phase was extracted with hydrochloric acid (2M, 5×200 mL). The pH of the strongly acidic aqueous phase was adjusted to 12-13 by slow addition of 35% aq. ammonia to reprecipitate the product. The aqueous phase was then reextracted with dichloromethane (3×300 mL). The crude organic extract was purified by passing through a short silica gel column (eluent: ethyl acetate). The eluted yellow solution was evaporated and the oily residue dried in vacuo to provide {4-[bis(2-hydroxyethyl)amino]phenyl}(phenyl)methanone (yellow-brown solid; 13.176 g; 62% yield).

$^1$H-NMR (400 MHz, $CDCl_3$): 7.72 (d, J=10.0 Hz, 2H), 7.69-7.66 (m, 2H), 7.53 (tt, J=8.2, 1.4 Hz, 1H), 7.42 (t, J=8.3 Hz, 2H), 6.55 (d, J=10.0 Hz, 2H), 4.22 (bs, 2H), 3.43 (t, J=5.4 Hz, 4H), 3.20 (t, J=5.4 Hz, 4H).

Large Scale Prep:

A 2000 mL two-neck flask was charged with 4-fluorobenzophenone (200.0 g; 1.00 mol) and diethanolamine (735.2 g; 7.00 mol). The flask was flushed with nitrogen, fitted with a reflux condenser and heated to 155° C. for 48 h under a gentle stream of nitrogen. Complete conversion of the starting 4-fluorobenzophenone was confirmed by TLC. After cooling to ambient temperature, the dark viscous reaction mass was diluted with ethyl acetate (2500 mL) and extracted with water (2000 mL). The organic phase was dried ($MgSO_4$), filtered and evaporated to give {4-[bis(2-hydroxyethyl)amino]phenyl}(phenyl)methanone (bright yellow powder; 260 g; 91% yield).

Example 4

4-{3-[bis(2-hydroxyethyl)amino]propoxy}-1-chloro-9H-thioxanthen-9-one

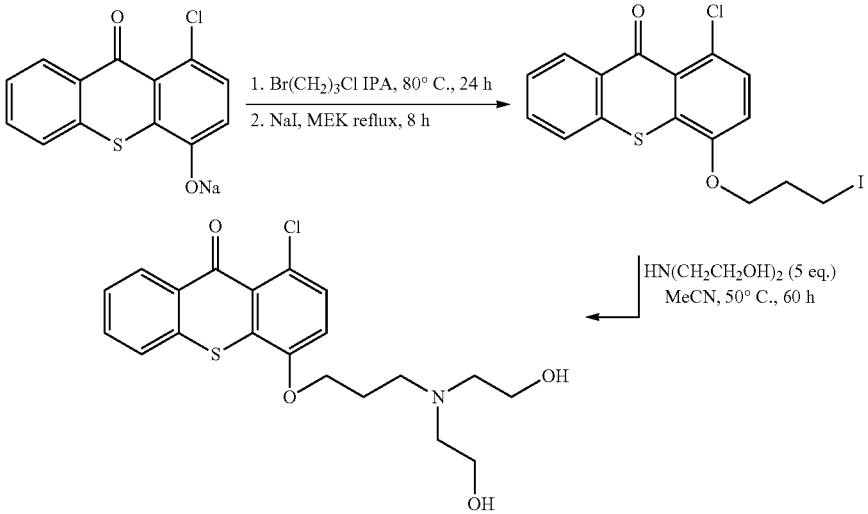

Small Scale Prep:

A 500 mL flask was charged with the sodium salt of 1-chloro-4-hydroxy-9H-thioxanthen-9-one (28.5 g; 0.100 mol), 1-bromo-3-chloropropane (17.4 g; 0.111 mol) and isopropyl alcohol (280 mL). The turbid reaction mixture was refluxed for 24 h. The hot solution was diluted with isopropyl alcohol (130 mL), drowned out in water (1400 mL) and the resulting suspension was extracted with dichloromethane (3×250 mL). The organic phase was separated, dried (MgSO$_4$), filtered and solvent removed in vacuo to give 1-chloro-4-(3-chloropropoxy)-9H-thioxanthen-9-one (24.4 g; 72% yield).

1-H NMR (400 MHz, CDCl$_3$): 8.39 (ddd, J=8.1, 1.5, 0.6 Hz, 1H), 7.54 (m, 1H), 7.48 (ddd, J=8.1, 1.4, 0.6 Hz), 7.41 (m, 1H), 7.33 (d, J=8.6 Hz, 1H), 6.92 (d, J=8.6 Hz, 1H), 4.23 (t, J=5.8 Hz, 2H), 3.83 (t, J=6.3 Hz, 2H), 2.32 (apparent quintet, J=6.0 Hz, 2H).

The crude product from the previous step (26.44 g; 77.94 mmol) was suspended in 2-butanone (250 mL) and sodium iodide (14.02 g; 93.52 mmol) was added. The reaction mixture was refluxed for 16 h. The reaction mixture was filtered, the solids were washed with boiling 2-butanone (2×50 mL), the filtrate evaporated, the oily residue dissolved in dichloromethane (300 mL) and extracted with water (2×100 mL). The organic phase was separated, evaporated and dried in vacuo to give crude 1-chloro-4-(3-iodopropoxy)-9H-thioxanthen-9-one (30.51 g; yellow solid; 91% yield).

1-H NMR (400 MHz, CDCl$_3$): 8.53 (dd, J=9.0, 1.4 Hz, 1H), 7.59 (m, 1H), 7.53 (dd, J=8.9, 1.5 Hz, 1H), 7.45 (m, 1H), 7.37 (d, J=9.6 Hz, 1H), 6.91 (d, J=9.6 Hz, 1H), 3.83 (t, J=6.3 Hz, 2H), 3.03 (t, J=7.4 Hz, 2H), 1.81 (apparent quintet, J=6.9 Hz, 2H).

Crude 1-chloro-4-(3-iodopropoxy)-9H-thioxanthen-9-one (10.0 g; 23.22 mmol) from the previous step was slowly charged into a solution of diethanolamine (14.65 g; 139.3 mmol) in acetonitrile (100 mL) heated to 50° C. The reaction mixture was stirred vigorously and heated to 50° C. for 60 h. The solvent was removed in vacuo and water (500 mL) was added. The mixture was extracted with dichloromethane (3×250 mL). The aqueous phase was discarded and the organic phase was extracted with hydrochloric acid (2M, 3×100 mL). The pH of the strongly acidic aqueous phase was adjusted to 12-13 by slow addition of 50% aq. NaOH to reprecipitate the product. The aqueous phase was reextracted with dichloromethane (4×100 mL), the organic phase dried (MgSO$_4$), evaporated to give 4-{3-[bis(2-hydroxyethyl)amino]propoxy}-1-chloro-9H-thioxanthen-9-one (5.31 g; 56% yield).

$^1$H-NMR (400 MHz, CDCl$_3$): 8.29 (ddd, J=8.1, 1.5, 0.6 Hz, 1H), 7.45 (ddd, J=8.2, 6.8, 1.4 Hz, 1H), 7.39 (ddd, J=8.1, 1.4, 0.6 Hz, 1H), 7.34 (ddd, J=8.2, 6.8, 1.4 Hz, 1H), 7.21 (d, J=8.6 Hz, 1H), 6.81 (d, J=8.6 Hz, 1H), 4.04 (t, J=6.1 Hz, 2H), 3.64 (bs, 2H), 3.59 (t, J=5.2 Hz, 4H), 2.73 (t, J=6.8 Hz, 2H), 2.63 (t, J=5.2 Hz, 4H), 1.94 (apparent quintet, J=6.4 Hz, 2H).

Large Scale Prep:

A 1000 mL three-neck flask was charged with 1-chloro-4-hydroxy-9H-thioxanthen-9-one (100.0 g; 0.381 mol), 1-bromo-3-chloropropane (71.9 g; 0.457 mol), anhydrous potassium carbonate (63.1 g; 0.457 mol) and 2-butanone (500 mL). The mixture was stirred at reflux for 60 h. Full conversion was confirmed by TLC. The reaction mixture was filtered through a glass sinter, the inorganic solids were washed with warm dichloromethane (4×100 mL). The filtrate was evaporated to dryness to give a bright yellow solid. The crude 1-chloro-4-(3-chloropropoxy)-9H-thioxanthen-9-one (129.1 g) was dissolved in 2-butanone (400 mL) and sodium iodide (62.8 g; 0.419 mol) was added. The reaction mixture was refluxed for 16 h, filtered hot, the solids were washed with boiling 2-butanone (2×100 mL) and the filtrate evaporated to dryness.

The crude product from the previous step was suspended in THF (300 mL) and the suspension was charged over 30 min to neat diethanolamine (240.1 g; 2.28 mol) at 60° C. The reaction was heated to reflux for 3 h. The clear yellow-brown solution was poured into water (2000 mL) and extracted with ethyl acetate (3×750 mL). The aqueous phase was discarded and the organic phase was extracted with hydrochloric acid (1M, 3×500 mL). The pH of the strongly acidic aqueous phase was adjusted to 12-13 by slow addition of 50% aq. NaOH to reprecipitate the product. The aqueous phase was reextracted with dichloromethane (4×500 mL), the organic phase dried (MgSO$_4$) and evaporated to dryness to give 4-{3-[bis(2-hydroxyethyl)amino]propoxy}-1-chloro-9H-thioxanthen-9-one (99.8 g; 64% yield).

Example 5

(2-{3-[bis(2-hydroxyethyl)amino]propoxy}-4-methoxyphenyl)(phenyl)methanone

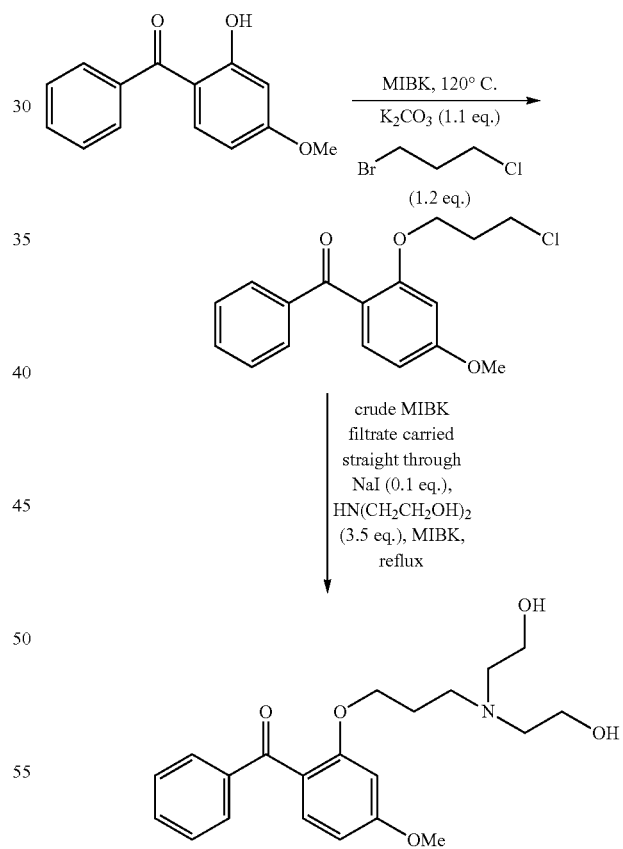

Large Scale Prep:

A 500 mL three-neck flask was charged with (2-hydroxy-4-methoxyphenyl)(phenyl) methanone (100.0 g; 0.4381 mol), 1-bromo-3-chloropropane (82.78 g; 0.5258 mol) and 4-methyl-2-pentanone (250 mL). Anhydrous potassium carbonate (66.61 g; 0.4819 mol) was added and the reaction mixture was stirred at reflux (120° C.) for 10 h. The reaction mixture was filtered hot and the inorganic solids were washed with 4-methyl-2-pentanone (2×100 mL). The filtrate was charged into a mixture of neat diethanolamine (161.2 g; 1.533 mol) and sodium iodide (6.57 g; 43.81 mmol). The reaction mixture heated to reflux (122° C.) for 24 h. The reaction mixture was cooled to room temperature and diluted with water (500 mL). The resulting emulsion was extracted with 4-methyl-2-pentanone (2×200 mL). The aqueous phase was discarded and the organic phase was extracted with 1 M HCl (2×500 mL). The aqueous phase was taken to pH 12 with 50% aqueous NaOH. The resulting emulsion was extracted with 4-methyl-2-pentanone (3×200 mL). The organic phase was separated, dried (MgSO$_4$), filtered and the solvent removed in vacuo. This provides (2-{3-[bis(2-hydroxyethyl)amino]propoxy}-4-methoxyphenyl)(phenyl)methanone (light yellow oil; 90.4 g; 55% yield over 3 steps).

$^1$H-NMR (400 MHz, CDCl$_3$): 7.68-7.66 (m, 2H), 7.44 (tt, J=7.4, 1.4 Hz, 1H), 7.37 (d, J=8.4 Hz, 1H), 7.35-7.32 (m, 2H), 6.48 (dd, J=8.5, 2.3 Hz, 1H), 6.42 (d, J=2.3 Hz, 1H), 3.83 (t, J=5.8 Hz, 2H), 3.77 (s, 3H), 3.57 (bs, 2H), 3.39 (t, J=5.3 Hz, 4H), 2.37 (t, J=5.3 Hz, 4H), 2.18 (t, J=7.1 Hz, 2H), 1.49 (apparent quintet, J=6.5 Hz, 2H).

Example 6

General Procedure the for Preparation of Polyurethanes in Solvent

A glass vial was charged with a reactive photoinitiator and a reactive polyether (amounts given in Table 1). The reaction vessel was heated to 120-130° C. under vacuum for 1 h to remove all moisture. The reaction vessel was then allowed to cool under vacuum, fitted with a reflux condenser and flushed with nitrogen. Dry chlorobenzene was added and the reaction was stirred at 60° C. to obtain a homogeneous clear solution with 30 wt % of solids. Appropriate amount of diisocyanate was added via syringe and the reaction mixture was heated under reflux for 16 h. The viscous yellow mixture was evaporated in vacuo, residual chlorobenzene was removed by co-evaporation with MeOH-water. The resulting gummy solid was dried in vacuo for 4-6 h at 75° C. This provided the appropriate polyurethane polymer as a light yellow-brown gummy solid.

Example 7

Solvent-Free Procedure the for Preparation of Polyurethanes

A glass vial was charged with a reactive photoinitiator and a reactive polyether (amounts given in Table 2). The reaction vessel was heated to 120-130° C. under vacuum for 1 h to remove all moisture. The flask was allowed to cool to 70° C. and charged with the appropriate amount of diisocyanate (given in Table 2). The reaction melt was then heated with stirring to 70° C. for 16 h. This provided the appropriate photochromic polymer as a white to light yellow solid.

TABLE 1

Composition and GPC characterisation of photochromic polyurethanes prepared in solvent

| reactive PI | wt % | reactive polyether | wt % | diisocyanate | wt % | polymer Mw | Mw/Mn |
|---|---|---|---|---|---|---|---|
| 4-{[bis(2-hydroxyethyl)amino]methyl}benzophenone | 2 | PEG-2000 | 85 | HMDI | 13 | 43 kDa | 2.37 |
| 4-{[bis(2-hydroxyethyl)amino]methyl}benzophenone | 10 | PEG-2000 | 72 | HMDI | 18 | 76 kDa | 2.12 |
| 4-{[bis(2-hydroxyethyl)amino]methyl}benzophenone | 2 | Jeffamine D-4000 | 90 | HMDI | 8 | 27 kDa | 1.75 |
| 4-{3-[bis(2-hydroxyethyl)amino]propoxy}benzophenone | 2 | PEG-2000 | 85 | HMDI | 13 | 76 kDa | 1.92 |
| 4-{3-[bis(2-hydroxyethyl)amino]propoxy}benzophenone | 10 | PEG-2000 | 73 | HMDI | 17 | 78 kDa | 2.27 |
| 4-{3-[bis(2-hydroxyethyl)amino]propoxy}benzophenone | 2 | Jeffamine D-4000 | 91 | HMDI | 7 | 35 kDa | 2.19 |
| 4-[bis(2-hydroxyethyl)amino]benzophenone | 2 | PEG-2000 | 85 | HMDI | 13 | 37 kDa | 1.87 |
| 4-[bis(2-hydroxyethyl)amino]benzophenone | 10 | PEG-2000 | 71 | HMDI | 19 | 34 kDa | 1.77 |
| 4-[bis(2-hydroxyethyl)amino]benzophenone | 2 | Jeffamine D-4000 | 90 | HMDI | 8 | 33 kDa | 2.09 |
| 4-{3-[bis(2-hydroxyethyl)amino]propoxy}-1-chloro-9H-thioxanthen-9-one | 2 | PEG-2000 | 85 | HMDI | 13 | 43 kDa | 1.76 |
| 4-{3-[bis(2-hydroxyethyl)amino]propoxy}-1-chloro-9H-thioxanthen-9-one | 10 | PEG-2000 | 74 | HMDI | 16 | 29 kDa | 1.62 |
| 4-{3-[bis(2-hydroxyethyl)amino]propoxy}-1-chloro-9H-thioxanthen-9-one | 2 | Jeffamine D-4000 | 91 | HMDI | 7 | 32 kDa | 2.06 |

TABLE 2

Composition and GPC characterisation of photochromic polyurethanes prepared under solvent-free conditions

| reactive PI | wt % | reactive polyether | wt % | diisocyanate | wt % | polymer Mw |
|---|---|---|---|---|---|---|
| 4{[bis(2-hydroxyethyl)amino]methyl}benzophenone | 2 | PEG-2000 | 89 | HDI | 9 | 54 kDa |
| 4{[bis(2-hydroxyethyl)amino]methyl}benzophenone | 2 | PEG-4600 | 93 | HDI | 5 | 50 kDa |
| 4-{3[bis(2-hydroxyethyl)amino]propoxy}benzophenone | 2 | PPG-2000 | 89 | HDI | 9 | 50 kDa |

TABLE 2-continued

Composition and GPC characterisation of photochromic polyurethanes prepared under solvent-free conditions

| reactive PI | wt % | reactive polyether | wt % | diisocyanate | wt % | polymer Mw |
|---|---|---|---|---|---|---|
| 4-{3[bis(2-hydroxyethyl)amino]propoxy}benzophenone | 2 | PPG-4000 | 93 | HDI | 5 | 45 kDa |
| 4-{3[bis(2-hydroxyethyl)amino]propoxy}benzophenone | 2 | PPG-2000 | 85 | HMDI | 13 | 24 kDa |
| 4-{3[bis(2-hydroxyethyl)amino]propoxy}benzophenone | 2 | PPG-4000 | 91 | HMDI | 7 | 21 kDa |
| 4-{3[bis(2-hydroxyethyl)amino]propoxy}benzophenone | 2 | PEG-2000 | 89 | HDI | 9 | 53 kDa |
| 4-{3[bis(2-hydroxyethyl)amino]propoxy}benzophenone | 2 | PEG-4600 | 94 | HDI | 4 | 62 kDa |

Example 8

UV Curing of Polyurethanes

A polyurethane was prepared from example 2 (2 wt % 4-{[bis(2-hydroxyethyl)amino]methyl}benzophenone, 85 wt % PEG 2000 and 13 wt % 4,4'-methylenebis(cyclohexyl isocyanate)) was processed to a plate using a heat press. A disc was cut from this plate (Ø25 mm) and placed in a plate-plate rheometer, where the bottom plate consists of a quartz window. Rheological properties were measured at 1 Hz at 120° C., where a UV-light source irradiating the polyurethane sample through the quartz plate was turned on at t=0 s. After approximately 100 s, the sample passes a transition from a liquid state to a solid state, i.e. a gel-point, which demonstrates that the photoinitiator moieties within the polyurethane are actually responsible for curing the sample when exposed to UV light.

Although the invention has been described with reference to a number of examples and reaction schemes, it should not be considered as limited by the above description. The full scope of the invention is defined by the appended claims.

The invention claimed is:

1. A polymeric photoinitiator, being a co-polymer of at least one monomer (A) with at least one monomer (B), wherein:

monomer (A) is a photoinitiator monomer (A) of the formula (I):

in which:

Pi is a photoinitiator moiety;

Z is a linker moiety selected from a single bond, optionally substituted $C_1$-$C_{12}$ alkylene, optionally substituted $C_1$-$C_{12}$ alkenylene, —O—, —S—, —NR$^1$—, —C(=O)—, —C(=NR$^1$)—, —SO$_2$—, —P(=O)(OR$^1$)—, optionally substituted heterocyclyl, optionally substituted aryl, —[O—($C_1$-$C_{12}$ alkylene)]$_n$-, —[NHR$^1$—($C_1$-$C_{12}$ alkylene)]$_n$, —[S—($C_1$-$C_{12}$ alkylene)]$_n$-, and combinations thereof; wherein R$^1$ is H or optionally substituted $C_1$-$C_{12}$ alkyl and n is an integer from 1-20;

$X_1$ and $X_2$ are independently selected from optionally substituted $C_1$-$C_{12}$ alkylene, optionally substituted $C_1$-$C_{12}$ alkenylene, optionally substituted heterocyclyl, —O—, —S—, —NR$^2$—, —C(=O)—, —C(=NR$^2$)—, —Si(R$^2$)$_2$—O—, optionally substituted aryl, and combinations thereof, wherein R$^2$ is H or optionally substituted $C_1$-$C_{12}$ alkyl;

wherein $X_1$ and $X_2$ or a part thereof may be linked to one another or to Z to form one or more ring structures;

wherein Z, $X_1$ and $X_2$ are selected such that N is a tertiary amine;

$W_1$ and $W_2$ are functional groups independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups;

monomer (B) comprises at least two functional groups $W_3$ and $W_4$, said $W_3$ and $W_4$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups, wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

2. A polymeric photoinitiator according to claim 1, wherein $W_1$ and $W_2$ are independently selected from alcohol, primary amine, secondary amine, or thiol groups.

3. A polymeric photoinitiator according to claim 1, wherein $W_1$ and $W_2$ are the same functional groups.

4. A polymeric photoinitiator according to claim 1, wherein $X_1$ and $X_2$ are independently selected from optionally substituted $C_1$-$C_{12}$ alkylene, —O—, —S—, —NR$^2$—, wherein R$^2$ is H or optionally substituted $C_1$-$C_{12}$ alkyl, and combinations thereof.

5. A polymeric photoinitiator according claim 1, wherein $X_1$ and $X_2$ may be linked to one another to form one or more ring structures.

6. A polymeric photoinitiator according to claim 1, wherein $X_1$ and $X_2$ are independently selected from optionally substituted $C_1$-$C_{12}$ alkylene.

7. A polymeric photoinitiator according to claim 1, wherein $X_1$ and $X_2$ are the same.

8. A polymeric photoinitiator according to claim 1, wherein Z is selected from a single bond, optionally substituted $C_1$-$C_{12}$ alkylene, optionally substituted $C_1$-$C_{12}$ alkenylene, —O—, —S—, —NR'—, —[O—($C_1$-$C_{12}$ alkylene)]$_n$-, wherein $R_1$ is H or optionally substituted $C_1$-$C_{12}$ alkyl and n is an integer from 1-20.

9. A polymeric photoinitiator according to claim 1, wherein Z is selected from optionally substituted $C_1$-$C_{12}$ alkylene.

10. A polymeric photoinitiator according to claim 1, wherein Z is selected from optionally substituted —O—($C_1$-$C_{12}$ alkylene)-, preferably optionally substituted —O—($C_1$-$C_6$ alkylene)-, optionally substituted —S—($C_1$-$C_{12}$ alkylene)-, preferably optionally substituted —S—($C_1$-$C_6$ alkylene)-, and optionally substituted —NR$^1$—($C_1$-$C_{12}$ alkylene)-, preferably optionally substituted —NR$^1$—($C_1$-$C_6$ alkylene)-, wherein R$^1$ is H or optionally substituted $C_1$-$C_{12}$ alkyl.

11. A polymeric photoinitiator according to claim 10, wherein Z is selected from optionally substituted —O—($C_1$-$C_{12}$ alkylene).

12. A polymeric photoinitiator according to claim 1, wherein Z is selected from a single bond, optionally substituted $C_1$-$C_6$ alkylene and optionally substituted —O—($C_1$-$C_6$ alkylene)-.

13. A polymeric photoinitiator according to claim 1, wherein Pi is a photoinitiator moiety selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acylphosphine oxides, phenyl ketocoumarins, silanes, camphorquinone, maleimides and derivatives thereof.

14. A polymeric photoinitiator according to claim 13, wherein Pi is a photoinitiator moiety selected from benzophenones, thioxanthones, benzilketals and phenyl hydroxyalkyl ketones, such as 2-hydroxy-2-methyl-1-phenylpropan-1-ones.

15. A polymeric photoinitiator according to claim 14, wherein Pi is a benzophenone having the general formula (V):

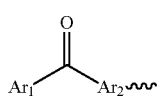

(V)

wherein Ar$_1$ and Ar$_2$ are independently selected from the same or different optionally substituted aryl, and where Z may be present at any position on Ar$_2$.

16. A polymeric photoinitiator according to claim 15, wherein Ar$_1$ and Ar$_2$ are both optionally substituted phenyl, preferably both phenyl, and where Z may be present at any position on Ar$_2$.

17. A polymeric photoinitiator according to claim 15, wherein where Z is present at the para-position on Ar$_2$.

18. A polymeric photoinitiator according to claim 1, wherein X$_1$ and X$_2$ are independently selected from optionally substituted $C_1$-$C_{12}$ alkylene, and W$_1$ and W$_2$ are —OH.

19. A polymeric photoinitiator according to claim 15, wherein the photoinitiator monomer (A) has the general formula (Ia):

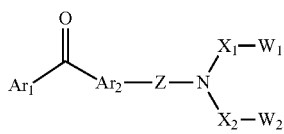

(Ia)

wherein Ar$_1$, Ar$_2$, Z, N, X$_1$, X$_2$, W$_1$ and W$_2$ are as defined in claim 15 and where Z may be present at any position on Ar$_2$.

20. A polymeric photoinitiator according to claim 19, wherein Ar$_1$ and Ar$_2$ are both optionally substituted phenyl, preferably both phenyl.

21. A polymeric photoinitiator according to claim 20, wherein Z is present at the para-position on Ar$_2$.

22. A polymeric photoinitiator according to claim 1, wherein the photoinitiator monomer (A) has the general formula (Ib):

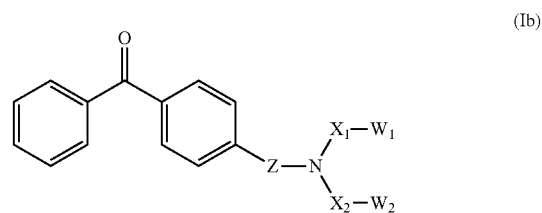

(Ib)

wherein Z, N, X$_1$, X$_2$, W$_1$ and W$_2$ are as defined in claim 1.

23. A polymeric photoinitiator according to claim 1, wherein the photoinitiator monomer (A) has the general formula (Ic):

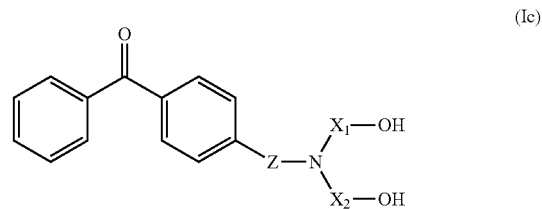

(Ic)

wherein Z, N, X$_1$, and X$_2$ are as defined in claim 1.

24. A polymeric photoinitiator according to claim 1, wherein photoinitiator monomer (A) is selected from the group consisting of:
{4-[bis(2-hydroxyethyl)amino]phenyl}(phenyl)methanone
(4-{[bis(2-hydroxyethyl)amino]methyl}phenyl)(phenyl)methanone
[4-({2-[bis(2-hydroxyethyl)amino]ethyl}sulfanyl)phenyl](phenyl)methanone
(4-{3-[bis(2-hydroxyethyl)amino]propoxy}phenyl)(phenyl)methanone
{4-[bis(2-hydroxypropyl)amino]phenyl}(phenyl)methanone
N,N-bis(2-hydroxyethyl)-2-(phenylcarbonyl)benzamide
N,N-bis(2-hydroxypropyl)-2-(phenylcarbonyl)benzamide
3,4-dihydroxy-1-[4-(phenylcarbonyl)phenyl]pyrrolidine-2,5-dione
N,N-bis[2-(methylamino)ethyl]-4-(phenylcarbonyl)benzamide
(4-{[bis(2-hydroxyethyl)amino]methyl}phenyl)[4-(phenylsulfanyl)phenyl]methanone
4-{3-[bis(2-hydroxyethyl)amino]propoxy}-1-chloro-9H-thioxanthen-9-one
4-[{2-[bis(2-hydroxyethyl)amino]ethyl}(methyl)amino]-1-chloro-9H-thioxanthen-9-one
2-[bis(2-hydroxyethyl)amino]ethyl [(9-oxo-9H-thioxanthen-2-yl)oxy]acetate 1-[bis(2-hydroxyethyl)amino]-4-propoxy-9H-thioxanthen-9-one
2-[(1-chloro-9-oxo-9H-thioxanthen-4-yl)oxy]-N,N-bis(2-hydroxyethyl)acetamide
1-{4-[bis(2-hydroxyethyl)amino]phenyl}-2-hydroxy-2-methylpropan-1-one
1-(4-{2-[bis(2-hydroxyethyl)amino]ethoxy}phenyl)-2-hydroxy-2-methylpropan-1-one
2-methyl-2-(morpholin-4-yl)-1-(4-{[bis(2-hydroxyethyl)amino]methyl}phenyl)propan-1-one, or
(3',5'-diisocyanatobiphenyl-4-yl)(phenyl)methanone.

25. A polymeric photoinitiator according to claim 1, wherein monomer (A) is selected from the group consisting of:
{4-[bis(2-hydroxyethyl)amino]phenyl}(phenyl)methanone
(4-{[bis(2-hydroxyethyl)amino]methyl}phenyl)(phenyl)methanone
(4-{3-[bis(2-hydroxyethyl)amino]propoxy}phenyl)(phenyl)methanone
{4-[bis(2-hydroxypropyl)amino]phenyl}(phenyl)methanone
N,N-bis(2-hydroxyethyl)-2-(phenylcarbonyl)benzamide
4-{3-[bis(2-hydroxyethyl)amino]propoxy}-1-chloro-9H-thioxanthen-9-one
2-[bis(2-hydroxyethyl)amino]ethyl [(9-oxo-9H-thioxanthen-2-yl)oxy]acetate
2-[(1-chloro-9-oxo-9H-thioxanthen-4-yl)oxy]-N,N-bis(2-hydroxyethyl)acetamide, or
1-{4-[bis(2-hydroxyethyl)amino]phenyl}-2-hydroxy-2-methylpropan-1-one.

26. A polymeric photoinitiator according to claim 1, wherein monomer (B) has the structure of formula II:

$$W_3\text{-}Q\text{-}W_4 \quad (II)$$

wherein $W_3$ and $W_4$ are defined as in claim 1 and wherein Q is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, optionally substituted biaryl, —[O—($C_1$-$C_{12}$ alkylene)]$_m$-, —[S—($C_1$-$C_{12}$ alkylene)]$_m$-, where m is an integer from 1-1000, and combinations thereof.

27. A polymeric photoinitiator according to claim 26, wherein Q is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl and optionally substituted biaryl.

28. A polymeric photoinitiator according to claim 26, wherein Q is selected from the group consisting of optionally substituted aryl and optionally substituted biaryl.

29. A polymeric photoinitiator according to claim 1, wherein $W_3$ and $W_4$ are independently selected from isocyanate and thioisocyanate groups.

30. A polymeric photoinitiator according to claim 1, wherein $W_3$ and $W_4$ are the same functional groups.

31. A polymeric photoinitiator according to claim 26, wherein monomer (B) is selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI), and 1,3-bis(isocyanato-methyl)cyclohexane (HXDI).

32. A polymeric photoinitiator according to claim 1, wherein—in the co-polymerization of monomers (A) and (B)—$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

33. A polymeric photoinitiator according to claim 1, wherein—in the co-polymerization of monomers (A) and (B)—$W_1$ reacts with $W_3$ to form a urethane, or thiourethane moiety, and $W_2$ reacts with $W_4$ to form a urethane or thiourethane moiety.

34. A polymeric photoinitiator according to claim 1, wherein both $W_1$ and $W_2$ are alcohol functional groups and both $W_3$ and $W_4$ are isocyanate functional groups.

35. A polymeric photoinitiator according to claim 1, further comprising one or more additional monomers (C), wherein each of said one or more additional monomers (C) comprises at least two functional groups $W_5$ and $W_6$, said $W_5$ and $W_6$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups, wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

36. A polymeric photoinitiator according to claim 35, wherein monomer (C) has the structure of formula III:

$$W_5\text{-}T\text{-}W_6 \quad (III)$$

wherein $W_5$ and $W_6$ are defined as in claim 35 and wherein T is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, optionally substituted biaryl, —[O—($C_1$-$C_{12}$ alkylene)]$_m$-, —[S—($C_1$-$C_{12}$ alkylene)]$_m$-, where m is an integer from 1-1000, and combinations thereof.

37. A polymeric photoinitiator according to claim 36, wherein T is selected from the group consisting of —[O—($C_1$-$C_{12}$ alkylene)]$_m$-, —[S—($C_1$-$C_{12}$ alkylene)]$_m$-, where m is an integer from 1-1000.

38. A polymeric photoinitiator according to claim 35, wherein $W_5$ and $W_6$ are independently selected from alcohol, primary amine, secondary amine, or thiol functional groups, preferably alcohol functional groups.

39. A polymeric photoinitiator according to claim 35, wherein $W_5$ and $W_6$ are the same functional groups.

40. A polymeric photoinitiator according to claim 35, wherein monomer (C) is selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton) diol, poly(1,6-hexanediol carbonate) and poly(ethylene terephthalate) diol.

41. A polymeric photoinitiator according to claim 1, wherein the weight ratio of monomers (A):(B) is 1:99-99:1.

42. A polymeric photoinitiator according to claim 35, wherein the weight ratio of monomers (A):(C) is 1:99-99:1.

43. A method for producing a polymeric photoinitiator, said method comprising step-growth co-polymerization of at least one monomer (A) with at least one monomer (B), wherein (A) and (B) have the structures described in claim 1.

44. A method according to claim 43, wherein the co-polymerization reaction additionally comprises one or more additional monomers (C), wherein each of said one or more additional monomers (C) comprises at least two functional groups $W_5$ and $W_6$, said $W_5$ and $W_6$ being independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups, wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

45. A method of cross-linking the polymeric photoinitiator of claim 1, said method comprising exposing the polymeric photoinitiator to UV radiation and/or heat.

\* \* \* \* \*